(12) United States Patent
Malberg

(10) Patent No.: US 8,795,375 B2
(45) Date of Patent: Aug. 5, 2014

(54) MODULAR NUCLEUS PULPOSUS PROSTHESIS

(75) Inventor: Marc I. Malberg, Princeton, NJ (US)

(73) Assignee: ResSpond Spinal Systems, Princeton, NJ (US)

( * ) Notice: Subject to any disclaimer, the term of this patent is extended or adjusted under 35 U.S.C. 154(b) by 998 days.

(21) Appl. No.: 12/508,356

(22) Filed: Jul. 23, 2009

(65) Prior Publication Data

US 2010/0023128 A1 Jan. 28, 2010

Related U.S. Application Data

(60) Provisional application No. 61/135,623, filed on Jul. 23, 2008.

(51) Int. Cl.
*A61F 2/44* (2006.01)
*A61F 2/30* (2006.01)
*A61F 2/46* (2006.01)

(52) U.S. Cl.
CPC ....... *A61F 2/442* (2013.01); *A61F 2002/30507* (2013.01); *A61F 2220/0075* (2013.01); *A61F 2220/0033* (2013.01); *A61F 2002/4627* (2013.01); *A61F 2002/448* (2013.01); *A61F 2310/00017* (2013.01); *A61F 2250/0015* (2013.01); *A61F 2002/30481* (2013.01); *A61F 2002/30563* (2013.01); *A61F 2002/30006* (2013.01); *A61F 2250/0018* (2013.01); *A61F 2002/30383* (2013.01); *A61F 2002/30461* (2013.01); *A61F 2220/0025* (2013.01); *A61F 2002/30604* (2013.01); *A61F 2310/00029* (2013.01); *A61F 2002/444* (2013.01); *A61F 2310/00023* (2013.01); *A61F 2002/30354* (2013.01)
USPC ....................................................... 623/17.16

(58) Field of Classification Search
USPC ............................................ 623/17.11–17.16
See application file for complete search history.

(56) References Cited

U.S. PATENT DOCUMENTS

| | | | |
|---|---|---|---|
| 3,867,728 A | 2/1975 | Stubstad et al. |
| 3,875,595 A | 4/1975 | Froning |
| 4,349,921 A | 9/1982 | Kuntz |
| 4,772,287 A | 9/1988 | Ray et al. |
| 4,904,260 A | 2/1990 | Ray et al. |
| 4,911,718 A | 3/1990 | Lee et al. |
| 4,917,704 A | 4/1990 | Frey et al. |
| 4,932,969 A | 6/1990 | Frey et al. |
| 4,955,908 A | 9/1990 | Frey et al. |

(Continued)

FOREIGN PATENT DOCUMENTS

| | | |
|---|---|---|
| DE | 197 10 392 C1 | 7/1999 |
| EP | 1925271 A1 | 5/2008 |

(Continued)

*Primary Examiner* — Matthew Lawson
(74) *Attorney, Agent, or Firm* — Law Offices of Robert F. Zielinski LLC

(57) ABSTRACT

At least two substantially identical generally mirror image complimentary disc segments combined to form a generally discoid endoprosthetic disc and associated tools and methods for replacing the intervertebral disc. Complimentary disc segments include outer circumferential walls roughly equal to a semi-circle aligned along concave-convex inner wall inner walls forming an "s"- shaped common border to provide a generally symmetrical discoid congruent structure which is positioned within the annulus of a spinal disc section. Disc segments may include structures to support, position and secure the segments to one another intradiscally. Surgical tools include structures for inserting and aligning disc members together. Also disclosed is a system and method for replacing the nucleus pulposus using the surgical tools adapted for placement and alignment of the disc.

15 Claims, 16 Drawing Sheets

(56) References Cited

U.S. PATENT DOCUMENTS

| | | |
|---|---|---|
| 5,041,114 A | 8/1991 | Chapman et al. |
| 5,047,055 A | 9/1991 | Bao et al. |
| 5,071,437 A | 12/1991 | Steffee |
| 5,123,926 A | 6/1992 | Pisharodi |
| 5,171,280 A | 12/1992 | Baumgartner |
| 5,171,281 A | 12/1992 | Parsons et al. |
| 5,192,326 A | 3/1993 | Bao et al. |
| 5,314,477 A | 5/1994 | Marnay |
| 5,401,269 A | 3/1995 | Buttner-Janz et al. |
| 5,443,514 A | 8/1995 | Steffee |
| 5,458,642 A | 10/1995 | Beer et al. |
| 5,458,643 A | 10/1995 | Oka et al. |
| 5,505,732 A | 4/1996 | Michelson |
| 5,507,816 A | 4/1996 | Bullivant |
| 5,522,899 A | 6/1996 | Michelson |
| 5,534,028 A | 7/1996 | Boa et al. |
| 5,545,229 A | 8/1996 | Parsons et al. |
| 5,549,679 A | 8/1996 | Kuslich |
| 5,556,431 A | 9/1996 | Buttner-Janz |
| 5,562,736 A | 10/1996 | Ray et al. |
| 5,571,189 A | 11/1996 | Kuslich |
| 5,593,409 A | 1/1997 | Michelson |
| 5,609,635 A | 3/1997 | Michelson |
| 5,645,597 A | 7/1997 | Krapiva |
| 5,674,294 A | 10/1997 | Bainville et al. |
| 5,674,295 A | 10/1997 | Ray et al. |
| 5,676,701 A | 10/1997 | Yuan et al. |
| 5,702,450 A | 12/1997 | Bisserie |
| 5,702,454 A | 12/1997 | Baumgartner |
| 5,716,415 A | 2/1998 | Steffee |
| 5,755,797 A | 5/1998 | Baumgartner |
| 5,772,661 A | 6/1998 | Michelson |
| 5,776,199 A | 7/1998 | Michelson |
| 5,824,093 A | 10/1998 | Ray et al. |
| 5,860,973 A | 1/1999 | Michelson |
| 5,865,846 A | 2/1999 | Bryan et al. |
| 5,893,889 A | 4/1999 | Harrington |
| 5,919,236 A | 7/1999 | Pfaff et al. |
| 5,984,967 A | 11/1999 | Zdeblick et al. |
| 6,001,130 A | 12/1999 | Bryan et al. |
| 6,039,763 A | 3/2000 | Shelokov |
| 6,096,038 A | 8/2000 | Michelson |
| 6,110,210 A | 8/2000 | Norton et al. |
| 6,146,422 A | 11/2000 | Lawson |
| 6,156,037 A | 12/2000 | LeHuec et al. |
| 6,156,067 A | 12/2000 | Bryan et al. |
| 6,159,211 A | 12/2000 | Boriani et al. |
| 6,187,048 B1 | 2/2001 | Milner et al. |
| 6,193,757 B1 | 2/2001 | Foley et al. |
| D439,162 S * | 3/2001 | Juhng ............................ D9/430 |
| 6,251,140 B1 | 6/2001 | Marino et al. |
| 6,258,125 B1 | 7/2001 | Paul et al. |
| 6,264,695 B1 | 7/2001 | Stoy |
| 6,302,914 B1 | 10/2001 | Michelson |
| 6,371,990 B1 | 4/2002 | Ferree |
| 6,387,130 B1 | 5/2002 | Stone et al. |
| 6,419,704 B1 * | 7/2002 | Ferree ........................ 623/17.12 |
| 6,423,083 B2 | 7/2002 | Reiley et al. |
| 6,443,988 B2 | 9/2002 | Felt et al. |
| 6,447,544 B1 | 9/2002 | Michelson |
| 6,468,311 B2 | 10/2002 | Boyd et al. |
| 6,482,234 B1 | 11/2002 | Weber et al. |
| 6,488,710 B2 | 12/2002 | Besselink |
| 6,533,818 B1 | 3/2003 | Weber et al. |
| 6,595,998 B2 | 7/2003 | Johnson et al. |
| 6,620,196 B1 | 9/2003 | Trieu |
| 6,652,587 B2 | 11/2003 | Felt et al. |
| 6,726,720 B2 | 4/2004 | Ross et al. |
| 6,726,721 B2 | 4/2004 | Stoy et al. |
| 6,733,535 B2 | 5/2004 | Michelson |
| 6,740,093 B2 | 5/2004 | Hochschuler et al. |
| 6,764,514 B1 | 7/2004 | Li et al. |
| 6,855,167 B2 | 2/2005 | Shimp et al. |
| 6,896,701 B2 | 5/2005 | Boyd et al. |
| 6,964,686 B2 | 11/2005 | Gordon |
| 7,001,431 B2 | 2/2006 | Bao et al. |
| 7,008,452 B2 | 3/2006 | Hawkins |
| 7,018,413 B2 | 3/2006 | Kruger |
| 7,267,690 B2 | 9/2007 | Felt |
| 7,270,679 B2 | 9/2007 | Istephanous et al. |
| 7,309,357 B2 | 12/2007 | Kim |
| 7,326,250 B2 | 2/2008 | Beaurain et al. |
| 7,503,933 B2 | 3/2009 | Michelson |
| 7,563,284 B2 | 7/2009 | Coppes et al. |
| 7,591,853 B2 | 9/2009 | Felt et al. |
| 7,695,515 B2 | 4/2010 | Sweeney |
| 7,731,753 B2 | 6/2010 | Reo et al. |
| 7,771,478 B2 | 8/2010 | Navarro et al. |
| 7,794,499 B2 | 9/2010 | Navarro et al. |
| 2002/0026244 A1 | 2/2002 | Trieu |
| 2002/0128715 A1 | 9/2002 | Bryan et al. |
| 2002/0183848 A1 | 12/2002 | Ray et al. |
| 2003/0055506 A1 | 3/2003 | Stoy et al. |
| 2003/0135279 A1 | 7/2003 | Michelson |
| 2003/0204260 A1 | 10/2003 | Ferree |
| 2003/0233146 A1 | 12/2003 | Grinberg et al. |
| 2004/0010318 A1 | 1/2004 | Ferree |
| 2004/0019354 A1 | 1/2004 | Johnson et al. |
| 2004/0054411 A1 | 3/2004 | Kelly et al. |
| 2004/0054413 A1 | 3/2004 | Higham et al. |
| 2004/0064144 A1 | 4/2004 | Johnson et al. |
| 2004/0098131 A1 | 5/2004 | Bryan et al. |
| 2004/0111155 A1 | 6/2004 | Ferree |
| 2004/0186576 A1 | 9/2004 | Biscup et al. |
| 2004/0220580 A1 | 11/2004 | Johnson et al. |
| 2004/0220672 A1 | 11/2004 | Shadduck |
| 2004/0230198 A1 | 11/2004 | Manzi et al. |
| 2004/0243241 A1 | 12/2004 | Istephanous et al. |
| 2004/0254643 A1 | 12/2004 | Jackson |
| 2005/0010290 A1 | 1/2005 | Hawkins |
| 2005/0015150 A1 | 1/2005 | Lee |
| 2005/0033437 A1 | 2/2005 | Bao et al. |
| 2005/0055097 A1 | 3/2005 | Grunberg et al. |
| 2005/0107880 A1 | 5/2005 | Shimp et al. |
| 2005/0154463 A1 | 7/2005 | Trieu |
| 2005/0154465 A1 | 7/2005 | Hodges et al. |
| 2005/0203599 A1 | 9/2005 | Garabedian et al. |
| 2005/0228400 A1 | 10/2005 | Chao et al. |
| 2005/0273178 A1 | 12/2005 | Boyan et al. |
| 2006/0106462 A1 | 5/2006 | Tsou |
| 2006/0142858 A1 | 6/2006 | Colleran et al. |
| 2006/0149381 A1 | 7/2006 | Kim |
| 2006/0167550 A1 | 7/2006 | Snell et al. |
| 2006/0189999 A1 | 8/2006 | Zwirkoski |
| 2006/0195191 A1 | 8/2006 | Sweeney, II et al. |
| 2006/0247778 A1 | 11/2006 | Ferree et al. |
| 2006/0247781 A1 * | 11/2006 | Francis ...................... 623/17.16 |
| 2006/0259144 A1 | 11/2006 | Trieu |
| 2006/0264965 A1 | 11/2006 | Shadduck et al. |
| 2006/0293756 A1 | 12/2006 | Felt |
| 2007/0027546 A1 | 2/2007 | Palm et al. |
| 2007/0032874 A1 | 2/2007 | Lee et al. |
| 2007/0073400 A1 | 3/2007 | Paul |
| 2007/0088362 A1 | 4/2007 | Bonutti et al. |
| 2007/0162130 A1 | 7/2007 | Rashbaum et al. |
| 2007/0244485 A1 | 10/2007 | Greenhalgh et al. |
| 2007/0265652 A1 | 11/2007 | Assell et al. |
| 2008/0039942 A1 * | 2/2008 | Bergeron ................... 623/17.16 |
| 2008/0046082 A1 | 2/2008 | Lee |
| 2008/0051902 A1 | 2/2008 | Dwyer |
| 2008/0058944 A1 * | 3/2008 | Duplessis et al. .......... 623/17.16 |
| 2008/0065220 A1 | 3/2008 | Alleyne et al. |
| 2008/0077153 A1 | 3/2008 | Pernsteiner et al. |
| 2008/0086142 A1 | 4/2008 | Kohm et al. |
| 2008/0114371 A1 | 5/2008 | Kluger |
| 2008/0119853 A1 | 5/2008 | Felt et al. |
| 2008/0133017 A1 | 6/2008 | Beyar et al. |
| 2008/0140086 A1 | 6/2008 | Moore et al. |
| 2008/0140206 A1 | 6/2008 | Felt |
| 2008/0208196 A1 | 8/2008 | Daum |
| 2008/0208343 A1 | 8/2008 | Felt |
| 2009/0125033 A1 | 5/2009 | Hushka et al. |

(56) References Cited

U.S. PATENT DOCUMENTS

| | | |
|---|---|---|
| 2009/0248159 A1 | 10/2009 | Aflatoon |
| 2010/0324689 A1 | 12/2010 | Obrigkeit et al. |
| 2011/0082555 A1 | 4/2011 | Martz et al. |

FOREIGN PATENT DOCUMENTS

| | | |
|---|---|---|
| WO | 2005067824 A1 | 7/2005 |
| WO | 2006116851 A1 | 11/2006 |
| WO | 2006127848 A2 | 11/2006 |

* cited by examiner

MODULAR NUCLEUS PULPOSUS PROSTHESIS

CROSS-REFERENCE TO RELATED PATENT APPLICATIONS

The present patent application claims the benefit of U.S. Provisional Patent Application Ser. No. 61/135,623, filed Jul. 23, 2008, the entirety of which is hereby incorporated by reference.

FIELD OF THE INVENTION

This invention relates generally to human prostheses, and more specifically to spinal column vertebral disc prostheses otherwise known as or referred to as spinal disc endoprostheses. The invention also relates to surgical tools and procedures for preparing the patient to receive a spinal disc endoprosthesis and for implanting the endoprosthesis in the patient's spine.

BACKGROUND OF THE INVENTION AND PRIOR ART

Intervertebral or spinal discs, lie between adjacent vertebrae which are the interlocking bones of the spine that are stacked on top of one another. Each disc forms a fibrocartilaginous joint to allow slight movement of the vertebrae, and acts as a ligament to hold the vertebrae together. Individual discs allow very limited vertebral motion such as extension and flexion; however, considerable motion is possible when several discs combine forces. In addition to providing the shock absorbing function, these discs allow the entire vertebrae or portions thereof to flex, bend, and twist.

In humans, there is one disc between each pair of vertebrae, except for the first cervical segment, the atlas. The atlas is a ring around the roughly cone-shaped extension of the axis or second cervical segment. The axis acts as a post around which the atlas can rotate, allowing the neck to swivel. There are a total of twenty-three discs in the human spine, which are most commonly identified by specifying the particular vertebrae they separate. For example, the disc between the fifth and sixth cervical vertebrae is designated "C5-C6", the disc between the fourth and fifth lumbar vertebrae would be "L4-L5" and so on.

Spinal discs consist of an outer annulus fibrosus, which surrounds the inner nucleus pulposus. The annulus fibrosus consists of several layers of fibrocartilage. The strong annular fibers of the capsule contain the nucleus pulposus and distribute pressure evenly across the disc. The nucleus pulposus contains loose fibers suspended in a mucoprotein gel having the consistency of jelly. The nucleus has a high water content (about 80-85%), with the remainder made up mostly of proteoglycan, type II collagen fibers and elastin fibers. The proteoglycan functions to trap and hold the water, which is what gives the nucleus its strength and resiliency.

The nucleus pulposus acts as a shock absorber, absorbing the impact of the body's daily activities and keeping the adjacent vertebrae separated, thus serving to protect the vertebrae, brain, and other structures such as the nerves extending from the spinal column. By analogy, the disc can be likened to a filled doughnut; the annulus fibrosis is similar to the dough and the nucleus pulposus is the jelly. If, for example, one presses down on the front of the doughnut the jelly moves posteriorly or to the back and vice versa. In the condition of a prolapsed disc, the jelly/nucleus pulposus is forced out of the doughnut/disc. In the partially deflated state, the adjacent vertebrae may put pressure on the spinal nerves located near the disc, causing chronic back pain, sciatica, numbness, weakness and other syndromes which often require surgical intervention.

Spinal discs can crack or rupture through aging, injury, and illness. For instance, as people age, the nucleus pulposus begins to dehydrate, which limits its ability to absorb shock. The annulus fibrosus gets weaker with age and begins to tear. While this may not cause pain in some people, in others one or both of these may cause chronic pain.

Spinal discs are structures that are, by and large, prone to degenerative changes associated with wear and tear aging, misuse (e.g. smoking) and repeated trauma, such as frequent heavy lifting as well as genetic predisposition. These degenerative changes can cause the loss of normal structure and/or function. Over time the collagen or protein structure of the annulus fibrosus weakens and may become structurally unsound. Additionally, both water and proteoglycans (i.e. molecules that attract water content) decreases. Age-related changes that cause degenerative disc disease include a loss of fluid in the discs and tiny tears or cracks in the annulus or capsule of the disc. A sudden or acute injury leading to a herniated disc may also begin the degeneration process. Stress from motion may also result in a disc problem (e.g. herniation). These changes are linked and lead to the disc's inability to handle mechanical stress and the breakdown of the discs can result in back or neck pain, weakness, and loss of function as well as osteoarthritis, herniated disc, or spinal stenosis.

One generally refers to the gradual dehydration of the nucleus pulposus as degenerative disc disease. Degenerative disc disease is somewhat of a misnomer in that it is not really a disease, but rather a degenerative cascade that at times can produce pain from a damaged disc. Degenerative disc disease can take place throughout the spine, but it most often occurs in the discs in the lumbar region and the cervical region. Herniation of a spinal disc and the often resultant symptoms of intractable pain, weakness, sensory loss, incontinence and progressive arthritis are among the most common of debilitating afflictions associated with this process. As used herein, degenerative disc disease will be understood to refer to all chronic or acute states of physical and physiological changes of the spinal discs resulting in pain or discomfort.

When the annulus fibrosus tears due to an injury or the aging process, the nucleus pulposus can begin to extrude through the tear. This is called disc herniation. Near the posterior side of each disc, all along the spine, major spinal nerves extend out to different organs, tissues, extremities etc. It is very common for the herniated disc to press against these nerves, commonly known as a pinched nerve, causing radiating pain, numbness, tingling, and diminished strength and/or range of motion.

In addition, the contact of the inner nuclear gel, which contains inflammatory proteins, with a nerve can also cause significant pain referred to as radicular pain or radiculitis. A common form of radiculitis is sciatica, a radicular pain that radiates along the sciatic nerve from the lower spine to the lower back, gluteal muscles, back of the upper thigh, calf, and foot as often secondary to nerve root irritation from a spinal disc herniation or from osteophytes in the lumbar region of the spine. Pain due to the inability of the dehydrating nucleus pulposus to absorb shock is called axial pain or disc space pain.

Herniated discs go by many names and these can mean different things to different medical professionals. A slipped disc, ruptured disc, or a bulging disc can all refer to the same medical condition.

Typically, patients suffering from degenerative disc disease, including disc herniation, may be treated conservatively through a regimen of pain medications, physical therapy, exercise, immobilization, acupuncture and combinations of the foregoing. In the case of a herniated disc, if a patient's condition does not improve after conservative treatment, and if there is clear physical evidence of nerve root or spinal cord compression apparent and confirmed through radiological means, surgical removal of the herniated disc may be indicated. The process of discectomy—as the name implies—involves the simple removal of the disc without attempt to replace or repair the malfunctioning unit.

Statistics suggest that surgical techniques such as discectomies, are likely to result in short-term relief, but will not prevent the progressive deterioration of the patient's condition in the long run. Through better pre-operative procedures and diagnostic studies, long-term patient results have improved somewhat. But it has become clear that unless the removed disc is replaced or the spine is otherwise properly supported, further degeneration of the patient's condition will almost certainly occur.

In the mid-1950's and 60's, Cloward and Smith & Robinson popularized anterior surgical approaches to the cervical spine for the treatment of cervical degenerative disc disease and related disorders of the vertebrae, spinal cord and nerve root; these surgeries involved disc removal followed by interbody fusion with a bone graft. It was noted by Robinson (Robinson, R. A.: The Results of Anterior Interbody Fusion of the Cervical Spine, J. Bone Joint Surg., 440A: 1569-1586, 1962) that after surgical fusion, osteophyte (bone spur) reabsorption at the fused segment might take place. However, it has become increasingly apparent that unfused vertebral segments at the levels above and below the fused segment degenerate at accelerated rates as a direct result of this fusion. This has led some surgeons to perform discectomy alone, without fusion, by a posterior approach in the neck of some patients. However, as has occurred in surgeries involving the lower back where discectomy without fusion is more common as the initial treatment for disc herniation syndromes, progressive degeneration at the level of disc excision is the rule rather than the exception. Premature degenerative disc disease at the level above and below the excised disc can and does occur.

Discectomy procedures have inherent risks since the portion of the disc to be removed is immediately adjacent the nerve root and any damage to the nerve root is clearly undesirable. Further, the long-term success of discectomy procedures is not always certain due to the loss of nucleus pulposus which can lead to a loss in disc height. Loss of disc height increases loading on the facet joints which can result in deterioration of the joint and lead to osteoarthritis and ultimately to foraminal stenosis, pinching the nerve root. Loss of disc height also increases the load on the annulus as well. As the annulus fibrosis has been shown to have limited healing capacity subsequent to discectomy. A compromised annulus may lead to accelerated disc degeneration which may require spinal interbody fusion or total disc replacement.

Spine surgery occasionally involves fusion of the spine segments. In addition to the problems created by disc herniation, traumatic, malignant, infectious and degenerative syndromes of the spine can be treated by fusion. Other procedures can include bone grafts and heavy duty metallic rods, hooks, plates and screws being appended to the patient's anatomy; often they are rigidly and internally fixed. None provide for a patient's return to near-normal functioning. Though these procedures may solve a short-term problem, they can cause other, longer term, problems.

A number of attempts have been made to solve some of the problems described above by providing a patient with spinal disc prostheses, or artificial discs of one sort or another.

For example, Steffee, U.S. Pat. No. 5,071,437, describes a spinal disc prosthesis having upper and lower rigid flat plates and a flat elastomeric core sandwiched between the plates. Frey et al., U.S. Pat. Nos. 4,917,704 and 4,955,908, disclose intervertebral prostheses, but the prostheses are described as solid bodies.

U.S. Pat. Nos. 4,911,718 and 5,171,281 disclose resilient disc spacers, but no inter-connective or containing planes or like elements are suggested, and sealing the entire unit is not taught.

U.S. Pat. No. 6,156,067 discloses an endoprosthesis having a resilient body formed of one or more materials which may vary in stiffness from a relatively stiff exterior annular gasket portion to a relatively supple central nucleus portion.

U.S. Pat. No. 6,964,686 discloses implantable intervertebral disc replacement prosthesis having a deformable flexure with disc member and lower and upper disc supports communicating with one another to provide support to the disc.

A more recent alternative to spinal fusion is replacement of the damaged disc with a motion preservation device, which includes either a nucleus or total disc replacement. The rationale for the development of the artificial disc is to prevent adjacent segment disease. Artificial disc devices can be broadly divided into two categories, those that replace the nucleus only, leaving the annulus and vertebral body end plates intact and those that involve replacement of the disc and addition of prosthetic end plates. Both strategies are directed at restoration of intervertebral disc function. Prosthetic nuclei are described, for example, in U.S. Pat. Nos. 5,047,055 and 5,192,326. United States Patent application US2002/0183848 also discloses a prosthetic spinal disc nucleus that has a hydrogel core surrounded by a constraining jacket.

There are also several different types of commercially available prosthetic devices for use in the cervical or lumbar segments of the spine designed for total disc replacement. For example, the Prodisc® and the Charite® disc are composites of cobalt chromium end plates with a polyethylene core. The Prodisc® is described in U.S. Pat. No. 5,314,477 and the Charite® disc is described in U.S. Pat. Nos. 5,401,269 and 5,556,431. The Prestige® disc is another type of artificial disc that comprises a metal on metal design with a ball and trough articulation. Another type of artificial disc that is gaining popularity in the cervical spine is the Bryan® disc, described in several United States Patent applications including 2004/0098131; 2004/0054411; and 2002/0128715. The Bryans disc is a composite artificial disc with a low friction, wear resistant, elastic nucleus that articulates with two circular metal plates.

It will be appreciated that prior art attempts at intervertebral endoprosthesis have inherent limitations and have been met with limited success. It will likewise be appreciated that there is a need to overcome the limitations of the prior art and to provide an intervertebral endoprosthesis that avoid the problems inherent in the known prior art.

It is an object of the present invention to provide a vertebral disc endoprosthesis which will perform effectively and efficiently within a patient's spine over a long period of time, and which will not encourage degeneration of or cause damage to adjacent natural disc parts.

It is another object to provide a vertebral disc endoprosthesis which does not require pins or other common mechanical hinge elements, yet which permits natural motion of the prosthetic parts and the adjacent natural anatomy.

It is a related objective to provide a new vertebral disc endoprosthesis surgical procedure which will decrease postoperative recovery time and inhibit post-operative disc, vertebral body and spinal joint degeneration.

Another object of the present invention is to provide an intervertebral disc prosthesis that assists in alleviating the symptoms of degenerative disc disease without sacrificing normal spinal biomechanics.

Yet another object of the present invention is a prosthesis that is easily implanted and mimics both the motion and the stiffness of a normal disc.

It is yet another object to provide a method of installing the endoprosthesis so as to accurately mate the endoprosthesis with a preexisting formed bone surface.

An associated object is to provide an endoprosthesis which will encourage bone attachment to, and growth upon, adjacent outer surfaces of the endoprosthesis.

Yet another object is to provide a vertebral endoprosthesis in which the parts are non-oncogenic.

Still another object is to provide a vertebral disc endoprosthesis having a resilient element to accommodate shocks and other forces applied to the spine.

Another object is to provide a highly effective vertebral endoprosthesis which includes several disc endoprostheses.

A related object is to provide these elements in a pre-assembled array for implantation in a patient.

Another object of the present invention is to provide tools and methods for inserting and positioning spinal disc members into a patient and may also include tools and methods for securing the spinal disc members together.

SUMMARY OF THE INVENTION

The present invention relates to a spinal disc endoprosthesis and to associated tools and methods for replacing the intervertebral disc. The endoprosthesis is generally discoid in appearance with rounded edge walls and has a segmented body formed of "yin-yang" shaped mirror imaged sections which facilitate limited lateral and twisting movement. The endoprosthesis may be fabricated of one or more materials which may vary in stiffness but are preferably of uniform stiffness and density. Preferred endoprosthetic materials include biocompatible metals such as orthopedic metal alloys, biocompatible ceramics, biocompatible silicone elastomers and combinations of the foregoing.

In one aspect, the present invention can comprise at least two complimentary spinal disc segments combined to form an endoprosthetic disc. In an embodiment, the complimentary segments are substantially identical with each having one-half of the familiar "yin-yang" shape including on one side, an outer circumferential wall with generally uniform "radius of curvature" roughly equal to a semi-circle and with each segment further having an inner wall (relative to the combined segments assembly) with a concave wall portion adjacent a convex wall portion and which is generally positioned along the diameter of the semi-circular arcs of the outer walls.

The spinal disc segments of the present invention are combined along their inner walls to share a common border and to form a generally congruent structure which is positioned within the annular ring structure or annulus of a spinal disc section which is to be replaced or repaired. As used herein, congruent means the completed generally symmetrical discord structure of the spinal endoprosthesis of the present invention formed of two or more disc segment members. Upon removal of the existing damaged nucleus pulposus and/or by occupying the space thereof, the complimentary spinal disc segments are inserted, positioned and secured preferably using tools specific to the individual segments. In this regard, and for ease of reference, the segments are surgically inserted one at a time with the initial segment being referred to herein as the first disc member and the following segment being referred to as the second disc member.

In other embodiments, each spinal disc segment may optionally further include a groove, notch, boss, conduit, channel, chamber and combinations thereof to support, position and secure the segments to one another after the segments are disposed intradiscally (i.e. within the annulus of the vertebral body in place of the nucleus pulposus) as well as to assist in the posterior surgical insertion and placement of the segments within a patient's vertebral column. The optional supporting, positioning and securing structures are exemplary and are not exhaustive. Other supporting, positioning and securing structures and devices including but not limited to elastomeric compounds, bio-compatible glues, bio-compatible fasteners, and magnets may also be employed to achieve the invention disclosed herein and are within the scope the appended claims.

In another aspect, the present invention can further comprise surgical tools to enable the intradiscal placement of the first and second disc members and to methods of use of said tools. In an embodiment, the tools include structures for detachably mounting the disc members and for placing the first and second members in alignment with each other and may also include structures for securing the first and second disc members together.

In yet another aspect, the present invention can comprise a system and method for replacing the nucleus pulposus with first and second disc members using the surgical tools adapted for the intradiscal placement of the first and second disc members, for placing the first and second members in alignment with each other and may also include methods of securing the first and second disc members to each other within the intradiscal space.

In use, a damaged disc is surgically removed and the replacement endoprosthesis is inserted between adjacent vertebral bodies in a patient's spine employing a surgical approach similar to a posterior lumbar interbody fusion.

Posterior lumbar interbody fusion (PLIF) is a surgical technique that involves removing a disc and fusing vertebrae together in the lower back (the lumbar region). The procedure involves a surgeon making an incision in the midline of the back. After cutting into the middle of the layer of muscle and ligament that sits on either side of the spine, the attachments to the spinous process and lamina are freed. Using a special instrument that removes small fragments of bone, the lamina is gradually removed until the surgeon can see the nerves. The nerves are then gently moved slightly to expose the disc between two vertebrae.

Using various instruments, an annulotomy is preformed and the nucleus pulposus is removed through the right or left sides of the spinal canal. A first disc member is then inserted into the annulus followed by a second disc member, the discs are aligned and secured to each other. The annulotomy is repaired and the space formerly filled with the nucleus pulposus being then occupied by the endoprosthetic disc of the present invention.

In an aspect of the invention, assemblies of endoprosthetic discs may be preconstructed. To implant the endoprosthesis assembly, information is obtained regarding the size, shape, and nature of a patient's damaged spine. Thereafter, one or more prosthetic disc units are selected and may also be constructed in conformity with that information. In another aspect of the invention, the completed and conformed disc assembly is implanted in the patient's spine.

These and other features, objects and advantages of the invention will become apparent to those persons skilled in the art upon reading the details of the invention as more fully described below.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE DRAWINGS

Before the subject devices, systems and methods are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

The present invention is directed to replacing the intervertebral disc, including the annulus and/or the nucleus, for treating or preventing further degeneration and/or herniation of the intervertebral disc by replacement. This is accomplished by implantation of one or more endoprosthetic discs of the present invention between one or more adjacent vertebral bodies.

Unless defined otherwise, all technical and scientific terms used herein have the same meaning as commonly understood by one of ordinary skill in the art to which this invention belongs. For example, the terms vertical and horizontal are used herein relative to a standing human being in the anatomical position. The terms "anterior", "posterior", "superior" and "inferior" are defined by their standard usage in anatomy; "anterior" refers to the region towards the front and the term "posterior" refers to the region towards the back. The term "sagittal" refers to regions on either side of the central midline axis of a standing human being; "superior" is upward toward the head; and "inferior" is lower or toward the feet. In the case of tools and apparatus, "distal" and "distally" are away from the body of the tool user and "proximal" and "proximally" are nearer or close to the body of the tool user.

The terms "upper" and "lower" are used herein to refer to the structure of the disc members as shown in the referenced drawings with respect to a reference position of the vertebrae on either side of the nucleus to be replaced. A "superior" vertebral body surface is the upper portion of a vertebral body onto which the spinal disc rests and an "inferior" vertebral body surface is the lower portion of a vertebra body positioned above the spinal disc of a functional spinal unit.

It will be appreciated that the focus of the invention is on those spinal discs found in the lumbar and lumbosacral regions of the spine; however, the invention here is not so limited and that adaptations and modifications can be made for use in the cervical spine and, much less frequently indicated, the thoracic spine.

Figure 1:
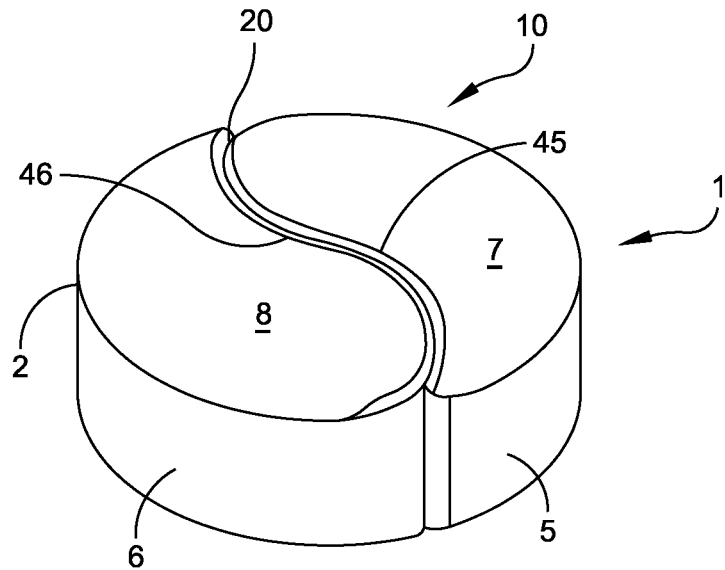
FIG. 1 shows a perspective view of an embodiment of an endoprosthetic disc of the present invention.

FIG. 1 shows one embodiment of endoprosthesis 10 comprising a pair of substantially identical complimentary disc members 1 and 2 in alignment along a common boundary 20 defined on their upper surfaces by inner wall shoulders 45, 47 and 46, 48 to form a generally congruent structure having a discoid shape. First disc member 2 includes side wall 6 and upper surface 8. Second disc member 1 includes side wall 5 and upper surface 7. As shown in the drawing, disc members 1 and 2 each have a shape substantially similar to one-half of the familiar "yin-yang" symbol and when combined in proper alignment, will combine to form a disc-like shape comprising two more or less equal halves. The shape of disc members 1 and 2 may also be generally referred to as a "fat-comma", "twisted tear-drop" and/or "paisley" shape and each term can be generally understood to refer to the shape substantially disclosed by the drawings and may be used interchangeably herein without departing from the spirit and scope of the invention.

Although not shown in the FIG. 1, it will be understood that disc members 1 and 2 have corresponding identically configured lower surface structures (not shown) opposite upper surfaces 7 and 8. Upper surface structures 7 and 8 (and corresponding lower surfaces, not shown) may also be slightly convexed relative to common boundary 20 to form a relatively constant curvature away from the body of endoprosthesis 10 so as facilitate better placement and physical wear characteristics of endoprosthesis 10 within the intraspinal space.

It will be understood that the endoprostheses of the present invention may be fabricated of metal, metal alloys, ceramics, plastics and combinations thereof. Particularly preferred metal alloys are orthopedic metal alloys specifically produced for the fabrication of artificial joints. These metal alloys have certain desirable characteristics, namely, strength, resilience and biocompatibility. Strength meaning that they will not break or permanently deform even under heavy constant loads; resilience meaning that they possess the requisite level of stiffness (e.g. too much stiffness will shield the spinal column too much from body weight); and, biocompatible meaning that they must be well tolerated by bone tissue.

Particularly useful orthopedic metal alloys include cobalt-chromium alloys, stainless steel alloys and titanium alloys all of which are well tolerated by bone tissue. Titanium alloys have particularly advantageous properties in that they have high strength, corrosion resistance and biocompatibility characteristics as compared to stainless steel and cobalt-chromium alloys.

Suitable plastics that may also be useful in the endoprostheses of the present invention may include medical-grade polyethylene commonly used on the surface of one implant that is designed to contact another implant. Polyethylene is very durable when it comes into contact with other materials. When a metal implant moves on a polyethylene surface, as it does, for example, in many joint replacements, the contact is very smooth and the amount of wear is minimal.

Figure 2:
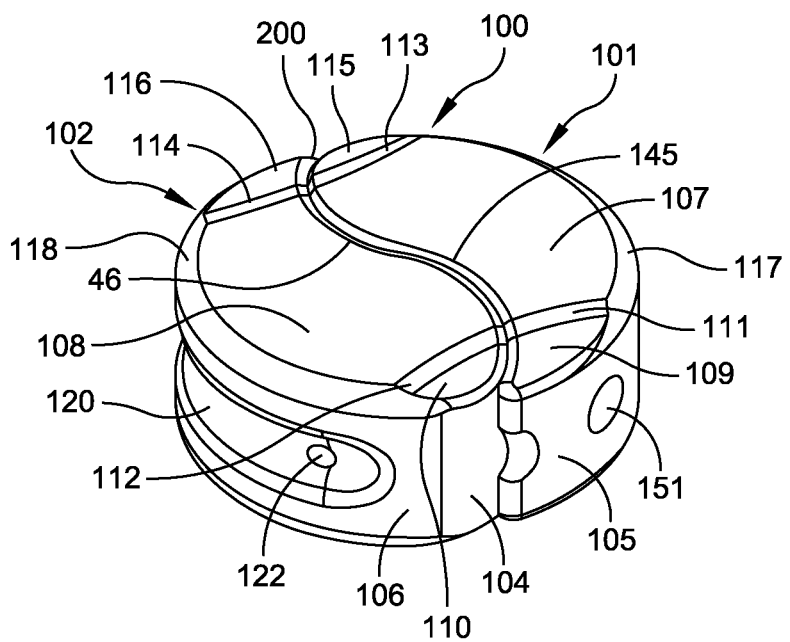
FIG. 2 shows a perspective view of an alternate embodiment of an endoprosthetic disc of the present invention.

FIG. 2 shows an embodiment of endoprosthesis 100 of the present invention. Endoprosthesis 100 comprises a pair of complimentary disc members 101 and 102 substantially identical on their upper and lower surfaces and which are in alignment along a common boundary 200 defined on their upper and lower surfaces by inner wall shoulders 145, 147 and 146, 148 to form a generally congruent structure having a discoid shape.

As shown in FIG. 2. disc members 101 and 102 each have surface shapes substantially similar to one-half of the familiar "yin-yang" symbol and when combined in proper alignment, will combine to form a disc-like shape comprising two more or less equal halves. With reference to FIG. 2 the shape of disc members 101 and 102 may also be generally referred to as a "fat-comma", "twisted tear-drop" and/or "paisley" shape and each term will be understood to refer to the shape substantially disclosed by FIG. 2 and may likewise be used interchangeably herein without departing from the spirit and scope of the invention. For reference purposes, the wider end portions of the first and second disc members may generally be referred to as the "head" or leading edge with the narrower end being referred to as the "tail" or trailing edge.

It will be also appreciated that with respect to embodiments of the invention disclosed in FIG. 2, first disc member 102 and second disc member 101 are designated as such with respect to one relative order of insertion and positioning of first and second disc members 102 and 101 and is not intended to be absolute designation of any particular order or sequence except for referential purposes with respect to the figures. It will likewise be appreciated that second disc member 101 can be inserted first with first disc member 102 being inserted second and vice versa.

First disc member 102 includes first disc member leading edge wall 104, first disc member outer side wall 106 and first disc member upper surface 108. Positioned above first disc member leading edge wall 104 is first disc member upper surface leading edge 110 and first disc member upper surface leading edge transition zone 112. First disc member upper surface leading edge transition zone 112 is positioned between and separates first disc member upper surface 108 from first disc member upper surface trailing edge transition zone 114 and first disc member upper surface trailing edge 116. As shown in FIG. 2, transition zones 112 and 114 are positioned on either side of first disc member upper surface 108. The transition zones generally define regions on upper surface 108 where the relative height of the upper surface diminishes to a slightly lower height (and therefore overall "thickness") as further defined by first disc member upper surface leading edge 110 and first disc member upper surface trailing edge 116. The relative positions of transition zones 112 and 114 are not absolute and in some embodiments may be moved forward or backwards relative to the positions shown in FIG. 2.

Positioned adjacent first disc member upper surface 108 is first disc member upper surface shoulder 118. Upper surface shoulder 118 may be a smooth rounded surface to improve overall fit and wear characteristics of endoprosthesis 100 and may be configured differently in other embodiments. Situated generally below upper surface shoulder 118 on first disc member outer side wall 106 is side wall notch 120. Side wall notch 120 may be a groove or depression adapted for receiving one embodiment of surgical tool or other apparatus for delivering first disc member 102 to a desired location. As shown in FIG. 2, located generally within side wall notch 120 is first disc member first suture channel 122. In other embodiments, first suture channel may be optionally present or may be positioned directly on side wall 106.

Second disc member 101 includes, second disc member outer side wall 105 and second disc member upper surface 107. Positioned distally on second disc member leading outer side wall 105 is second disc member leading edge (not shown) above which is second disc member upper surface leading edge 115 and second disc member upper surface leading edge transition zone 113. Second disc member upper surface leading edge transition zone 113 is positioned between and separates second disc member upper surface 107 from second disc member upper surface trailing edge transition zone 111 and second disc member upper surface trailing edge 109. As shown in FIG. 2, second disc member transition zones 111 and 113 are positioned on either side of second disc member upper surface 107. As in the case of first disc member 102, second disc member transition zones 111 and 113 generally define regions on upper surface 107 where the relative height of the upper surface diminishes to a slightly lower height (and therefore overall "thickness") as further defined by second disc member upper surface leading edge 115 and second disc member upper surface trailing edge 109. The relative positions of second disc member transition zones 111 and 115 are not absolute and in some embodiments may be moved forward or backwards relative to the positions shown.

Positioned adjacent second disc member upper surface 107 is second disc member upper surface shoulder 117. Upper surface shoulder 117 may be a smooth rounded surface to improve overall fit and wear characteristics of endoprosthesis 100 and may be configured differently in other embodiments. Situated generally below second disc member trailing edge on second disc member outer side wall 105 is insertion guide orifice 151. Insertion guide orifice 151 may be a channel or bore adapted for receiving one embodiment of surgical tool or other apparatus for delivering second disc member 101 to a desired location intradiscally preferably adjacent first disc member 102.

Although not shown in the FIG. 2, disc members 101 and 102 have corresponding identically configured lower surfaces (not shown) opposite upper surfaces 107 and 108. Upper surfaces 107 and 108 (and corresponding lower surfaces, not shown) may also be slightly convexed relative to the cross section of endoprosthesis 100 to form a relatively constant curvature away from the body of endoprosthesis 100 so as facilitate better placement and physical wear characteristics of endoprosthesis 100 within the intraspinal space.

Figure 3:
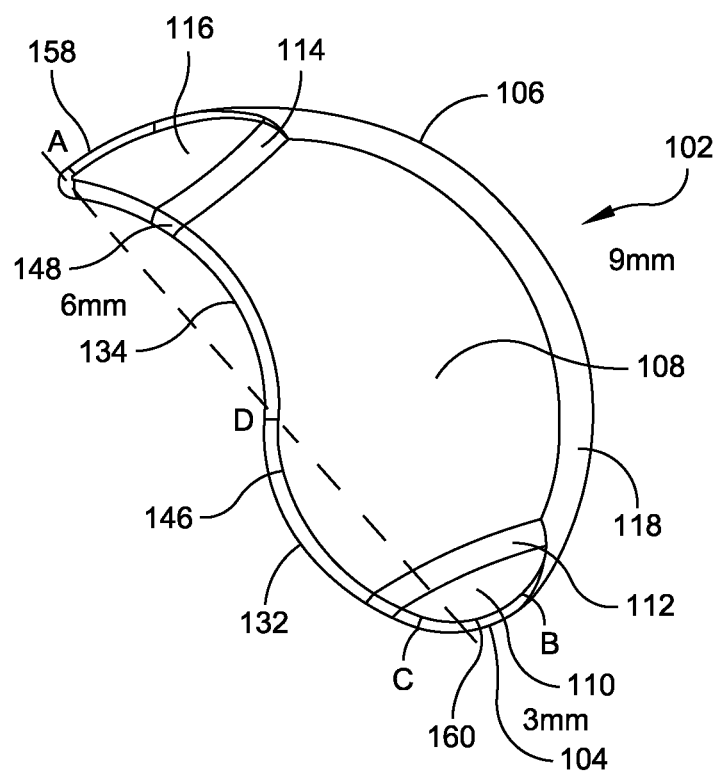
FIG. 3 shows a top view of a first disc segment of the embodiment shown in FIG. 2.

Referring now to FIG. 3, there is shown a top plan view of first disc member 102. As may be appreciated from the drawing, first disc member has a shape substantially similar to one-half of the "yin-yang" symbol generally defined a continuous upper and lower periphery and further defined by outer wall shoulder 118, leading edge shoulder 160, convex inner wall shoulder 146, concave inner wall shoulder 148 and trailing edge shoulder 158.

Outer wall 106 may be generally defined as a semi-circular arc having a relatively constant radius of curvature defined by the line A-B. Contiguous with outer wall 106 is leading edge wall 104 having a radius of curvature less than outer wall 106. Leading edge wall 104 may be generally defined by the line B-C. Contiguous with leading edge wall 104 is inner wall convex wall 132 having a radius of curvature that may be generally defined by line C-D. Contiguous with inner convex wall 104 is inner concave wall 134 which in turn is more or less contiguous on the end opposite inner convex wall 132 with outer wall 106 and is generally defined by the line D-A. Inner convex wall 132 and inner concave wall 134 will generally have similar radii of curvature in opposite directions, which is to say that inner convex wall 132 will extend away from the body of first disc member 102 while inner concave wall will extend towards the body of first disc member 102. For example, in an embodiment, outer wall 106 may have a radius of curvature of approximately 9 mm, leading edge wall may have a radius of curvature of about 3 mm and inner convex and inner concave walls may each have a radius of curvature roughly 6 mm. It will also be appreciated that the peripheral wall of first disc member may further include additional areas having a smaller radius of curvature at or near point A, for example, to create a more rounded tail portion end of the one-half "yin-yang" shape.

FIG. 3 shows first disc member upper surface 108 more or less situated centrally on the upper surface of first disc member 102. Generally positioned between first disc member upper surface 108 and outer wall 106 is shoulder 118. In the embodiment shown shoulder 118 may be a generally uniform rounded edge to facilitate fit and wear of the endoprosthesis of the present invention when inserted intradiscally; however, it will also be appreciated that the shoulder 118 may be optionally absent or non-uniform in its configuration and may take other forms with a greater or lesser rounded edge surface. Positioned towards the head portion of first disc member 102 are first disc member upper surface leading edge 110 and first disc member upper surface leading edge transition zone 112. First disc member upper surface leading edge transition zone 112 is positioned between first disc member upper surface 108 and first disc member leading edge surface. Positioned posteriorly on the first disc member upper surface 108 towards the tail end of first disc member 102 are upper surface trailing edge transition zone 114 and first disc member upper surface trailing edge 116. On the peripheral wall opposite shoulder 108 is inner shoulder 146 which may extend more or less from the upper leading edge surface 110 to upper leading trailing edge surface 116.

As will be appreciated by the figures transition zones 112 and 114 are positioned on either side of first disc member upper surface 108. The transition zones generally define regions on upper surface 108 where the relative height of the upper surface diminishes to a slightly lower height (and therefore overall "thickness" in cross section) as further defined by first disc member upper surface leading edge 110 and first disc member upper surface trailing edge 116. The relative positions of transition zones 112 and 114 are not absolute and in some embodiments may be moved forward or backwards relative to the positions shown in FIG. 3. It will likewise be appreciated that the lower surfaces (not shown) of first disc member 102 will be substantially identical in form and function to the structures and reference points generally described with respect to the upper surfaces and peripheral walls.

Figure 4:
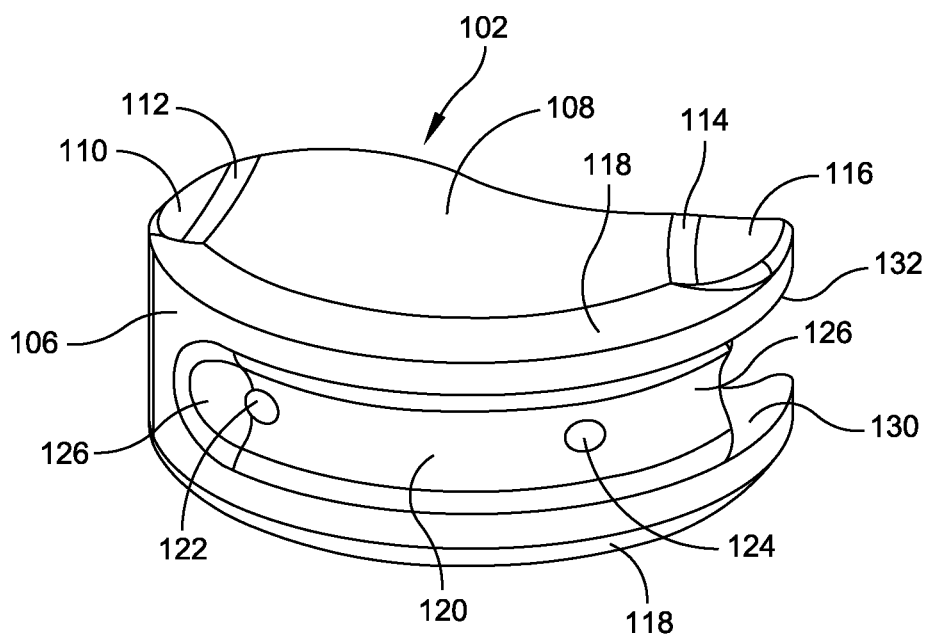
FIG. 4 shows an outer side perspective view of the first disc segment of the embodiment shown in FIG. 3.

FIG. 4 is an outer side perspective view of an embodiment of the first disc member of FIG. 2. Situated generally below upper surface shoulder 118 and within first disc member outer side wall 106 is side wall notch 120. Side wall notch 120 may be a groove or depression adapted for receiving one embodiment of surgical tool or other apparatus for delivering first disc member 102 to a desired position within the annulus of a spinal disc. Side wall notch 120 may also take other forms such as an orifice or a series of orifices which into which may be received a surgical tool or other similar device to aide in delivering and positioning first disc member 102. Located generally within side wall notch 120 are first disc member first suture channel 122 and first disc member second suture channel 124. It will be understood that first and second suture channels are boxes forming passageways that extend from the outer surface of the disc member through the disc member to the inner surface of the disc member. The outer surface numeral designations will appear as whole numbers whereas the inner surface designations will appear as the corresponding number with the "'" designation (e.g., 122', 124'). In other embodiments, side wall groove may be absent and first and second suture channels may be optionally present or may be positioned directly on side wall 106.

Side wall notch 120 may be generally defined by side wall notch head 126 and side wall notch tail 128. Positioned away from side wall notch tail 128 is inner notch floor 130. As will be appreciated from FIG. 4 and well as FIGS. 5 and 6, discussed more fully below, the upper and lower surfaces of first disc member 102 are essentially mirror images, which is to say that the structures, surfaces and proportions of the upper and lower portions of the first disc segment are identical as measured by a longitudinal cross sectional line positioned through its central axis.

Figure 5:
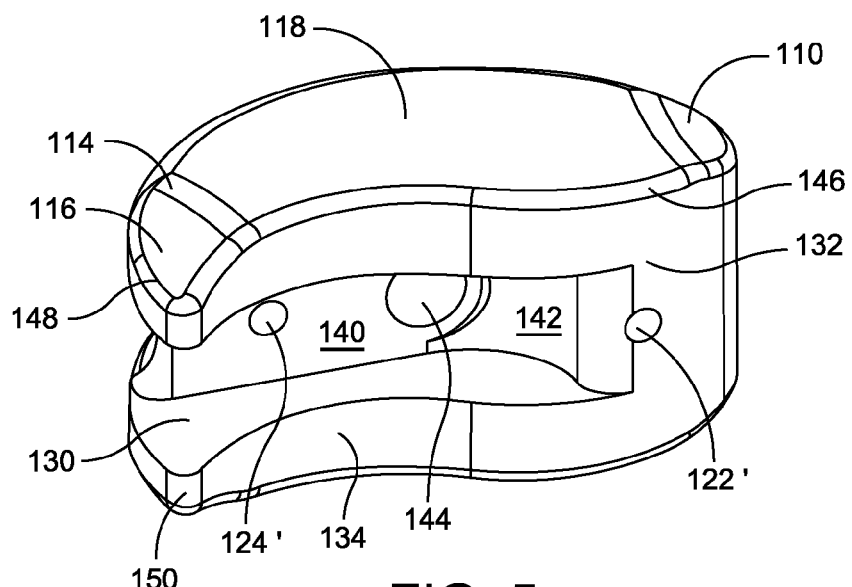
FIG. 5 is an inner side perspective view of the first disc segment of the embodiment shown in FIG. 3.

FIG. 5 is an inner wall perspective view of the first disc member shown in FIG. 4. First disc member upper surface 108 is shown having first disc member upper leading edge surface 110 towards the head portion and first disc member trailing edge surface 116 towards the tail portion of first disc member 102. Positioned on the inner peripheral edge of first disc member 102 are inner wall shoulders 146 and 148 defining in general, a continuous boundary between upper surface 108 and inner convex wall 132 and between upper surface 108 and inner concave wall 134. Inner shoulder 146 may extend more or less from the upper leading edge surface 110 to upper trailing edge surface 116 at tail wall 150. Positioned adjacent inner shoulder 146 on upper trailing edge surface is the continuation of inner concave wall shoulder 148 which extend on the periphery until it transitions into outer shoulder 118.

Situated within inner convex wall 132 and inner concave wall 134 is inner notch 140 defined on one end by inner notch convex end 142 and by side wall notch tail 128 on its opposite end. Inner notch 140 is further defined by inner notch floor 130 and inner notch ceiling 132. Located within inner notch 140 is threaded screw aperture 144. Threaded screw aperture 144 is generally centrally disposed within the body of first disc segment 102 and is adapted to mateably receive a threaded screw or other fastening means as will be discussed in the figures below. In other embodiments, threaded screw aperture may be repositioned or may be absent. Positioned on either side of threaded screw aperture 144 and roughly equidistant from the center of aperture 144 are first member first suture channel 122' and first member second suture channel 124'. As used herein the "'" designation will refer to the corresponding suture channel orifice on the inner wall of first disc member 102.

Figure 6:
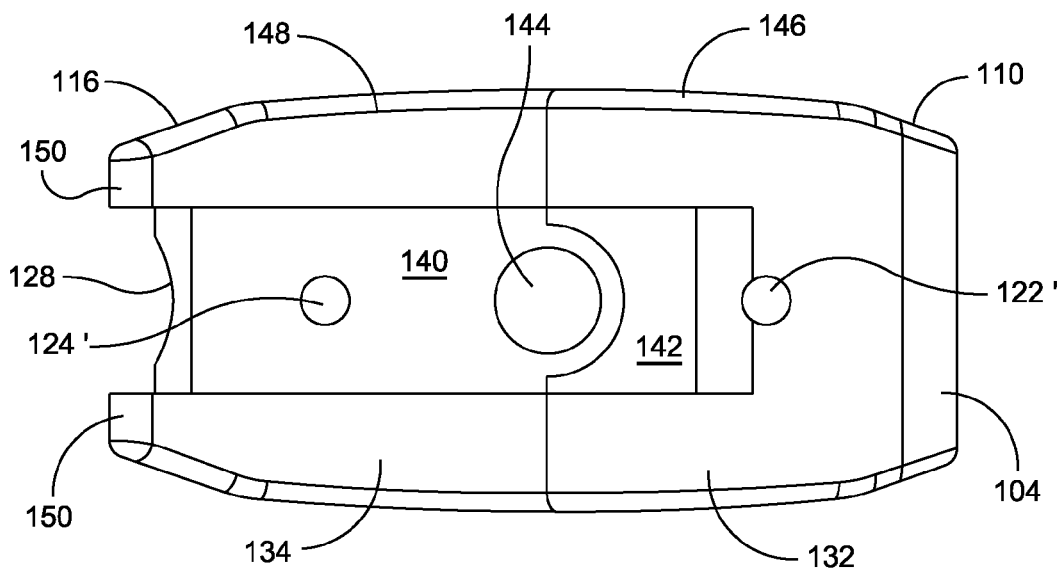
FIG. 6 is an inner side view of the first disc segment of the embodiment shown in FIG. 3.

FIG. 6. is a side perspective view of first disc member 102 as shown in FIGS. 4 and 5. The slightly convexed shape of first disc member may be seen with respect to the mirror imaged upper surfaces identified in FIGS. 2 though 5 and the lower surfaces. Inner wall shoulders 146 and 148 respectively define a continuous boundary between upper surface 108 and inner convex wall 132 and between upper surface 108 and inner concave wall 134. Inner shoulder 146 and 148 may extend more or less from the upper leading edge surface 110 to upper trailing edge surface 116 at tail wall 150.

Inner notch 140 is defined on one end by inner notch convex end 142 and by side wall notch tail 128 on its opposite end. Inner notch 140 is further defined by inner notch floor 130 and inner notch ceiling 132. It will be appreciated however that the terms floor and ceiling are for reference purposes with respect to their positions shown in FIG. 6 inasmuch as the figure and the first disc member itself may be rotated 180° in which case the floor becomes the ceiling and vice versa. Located within inner notch 140 is threaded screw aperture 144. Threaded screw aperture 144 is generally centrally disposed mid-line within the body of first disc segment 102. Positioned on either side of threaded screw aperture 144 and roughly equidistant from the center of aperture 144 are first member first suture channel 122' and first member second suture channel 124'. In the embodiment shown in FIG. 6, first member first suture channel is located on the peripheral edge of inner notch convex end 142.

Figure 7:
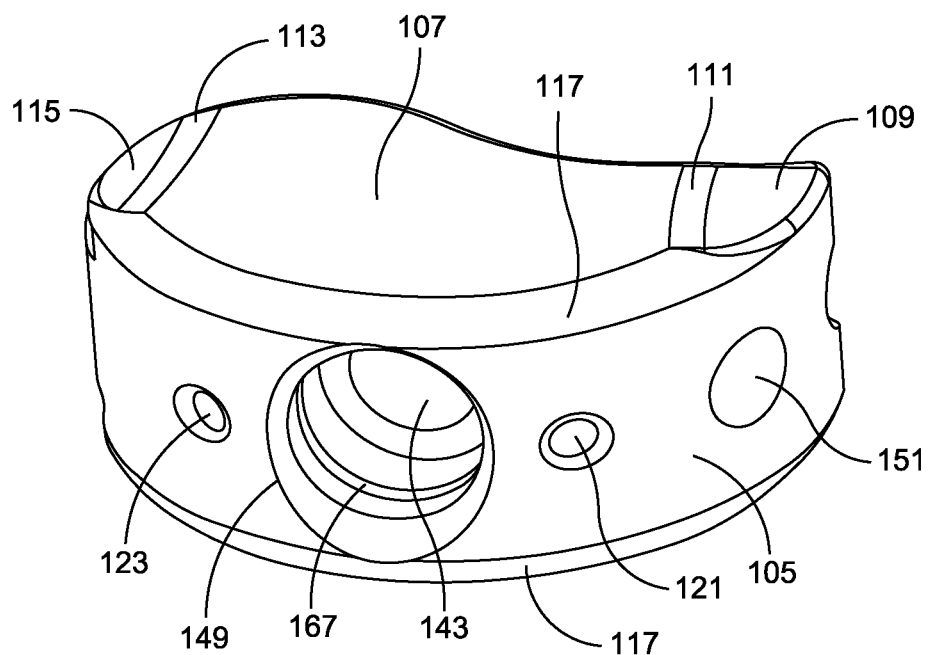
FIG. 7 is an outer side perspective view of an embodiment of a second disc segment shown in FIG. 2.

FIG. 7 is an outer side perspective view of an embodiment of the second disc member of FIG. 2. Second disc member upper surface 107 more or less situated centrally on the upper surface of second disc member 101. Generally positioned between second disc member upper surface 107 and outer wall 105 is shoulder 117. In the embodiment shown shoulder 117 may be a generally uniform rounded edge to facilitate fit and wear of the endoprosthesis of the present invention when inserted intradiscally; however, it will also be appreciated that the shoulder 117 may be optionally absent or non-uniform in its configuration and may take other forms with a greater or lesser rounded edge surface. Positioned towards the head portion of second disc member 101 is second disc member upper surface leading edge 115 and second disc member upper surface leading edge transition zone 113. Second disc member upper surface leading edge transition zone 113 is positioned between second disc member upper surface 107 and second disc member leading edge surface 115. Positioned posteriorly on the second disc member upper surface 107 towards the tail end of second disc member 101 is upper surface trailing edge transition zone 111 and second disc member upper surface trailing edge 109. On the peripheral wall opposite shoulder 107 is inner shoulder 145 which may extend more or less from the upper leading edge surface 115 to upper leading trailing edge surface 109.

As will be appreciated from the figures, transition zones 111 and 113 are positioned on either side of second disc member upper surface 107. The transition zones generally define regions on second member upper surface 107 where the relative height of the upper surface diminishes to a slightly lower height (and therefore overall "thickness" in cross section) as further defined by second disc member upper surface leading edge 115 and second disc member upper surface trailing edge 109. As in the case of first disc member 102, the relative positions of transition zones 111 and 113 are not absolute and in some embodiments may be moved forward or backwards relative to the positions shown in FIG. 7; however it will understood that the relative positions of the transition zones of the second disc member will generally correspond to the placement of the transition zones on a first disc member. It will likewise be appreciated that the lower surfaces (not shown) of second disc member 101 will be substantially identical in form and function to the structures and reference points generally described with respect to the upper surfaces and peripheral walls.

Situated generally below upper surface shoulder 117 and within second disc member outer side wall 105 are screw aperture 143, screw lock ring 167 and screw recess 149. Positioned at approximately 90° with respect to the bore of screw aperture 143 is inserter pin orifice 151. Inserter pin orifice 151 may be a cavity or chamber adapted for receiving one embodiment of surgical tool or other apparatus for delivering second disc member 101 to a desired position within the annulus of a spinal disc. Inserted pin orifice 151 may also take other forms such as an groove, slot or a series of orifices which into which may be received a surgical tool or other similar device to aide in delivering and positioning second disc member 101. Located generally within second member side wall 105 is second disc member first suture channel 121 and second disc member second suture channel 123.

Figure 8:
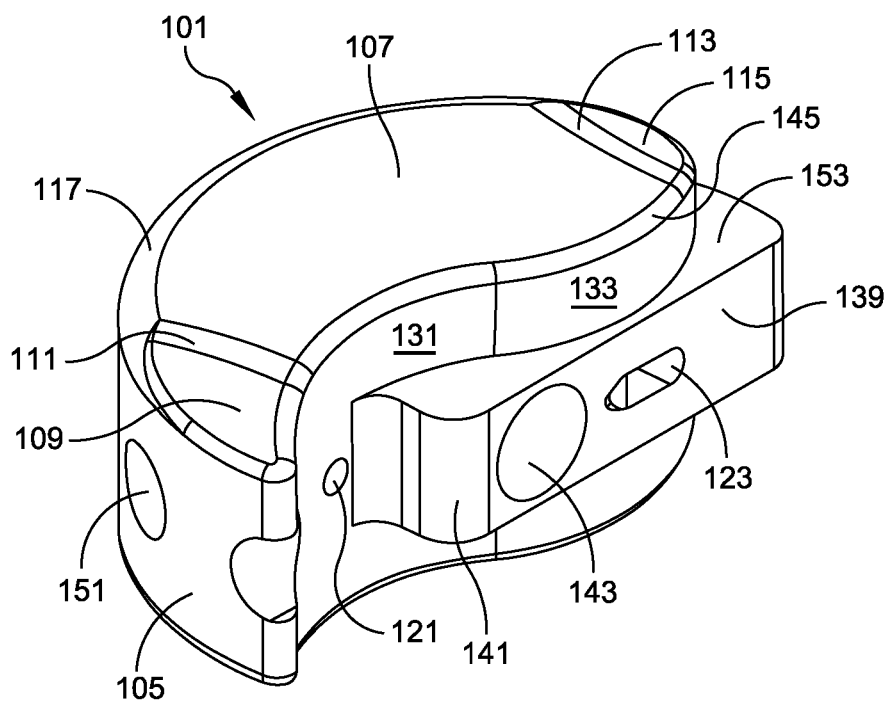
FIG. 8 is an inner side perspective view of an embodiment of the second disc segment shown in FIG. 7.

FIG. 8 is an inner wall perspective view of the second disc member shown in FIG. 7. Second disc member upper surface 107 is shown having second disc member upper leading edge surface 115 towards the head portion and second disc member trailing edge surface 109 towards the tail portion of second disc member 101. Positioned on the inner peripheral edge of second disc member 101 are inner wall shoulders 145 and 147 defining in general, a continuous boundary between upper surface 107 and second disc member inner convex wall 133 and between upper surface 107 and inner concave wall 131. Inner shoulders 145 and 147 may extend more or less from second disc member upper leading edge surface 115 to upper trailing edge surface 109 at second disc member tail wall 161. Positioned adjacent inner convex wall shoulder 145 on upper trailing edge surface is inner concave well shoulder 147 which extend on the periphery until it transitions into outer shoulder 117.

Situated within inner convex wall 132 and inner concave wall 134 is boss 139 defined on one end by inner notch concave end 141 and by second disc member side wall notch tail 157 on its opposite end. Inner notch 140 is further defined by boss floor 153 and boss ceiling (not shown). Located within boss 139 is screw aperture 143. Screw aperture 143 is generally centrally disposed within the body of second disc segment 101 and is adapted to mateably receive a screw or other fastening means to secure second disc segment 101 to a first disc segment. In other embodiments, screw aperture may be repositioned or may be absent. Positioned on either side of screw aperture 143 and roughly equidistant from the center of aperture 143 is second member first suture channel 121' and second member second suture channel 123'. As in the case of first disc member 102, first and second suture channels are bones having passageways with outer wall openings and inner wall openings. The inner openings are identified using the "'" designations, (e.g., 121' and 123') whereas corresponding outer openings are identified without the designation (i.e., 121 and 123).

Figure 9:
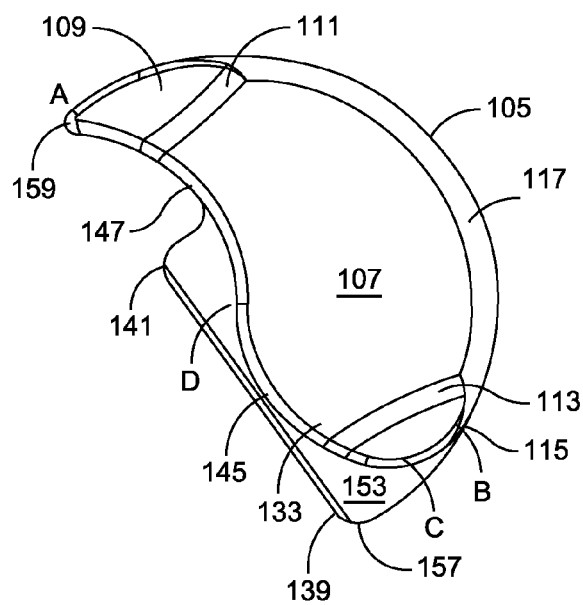
FIG. 9 is a top view of a second disc segment of the embodiment shown in FIG. 7

Referring now to FIG. 9, there is shown a top plan view of second disc member 101 shown in FIGS. 7 and 8. Second disc member 101 include upper and lower surface shapes substantially similar to one-half of the "yin-yang" symbol generally defined by a continuous upper and lower periphery and further defined by outer wall shoulder 117, leading edge shoulder 125, convex inner wall shoulder 145, concave inner wall shoulder 147 and trailing edge shoulder 159.

Outer wall 105 of second disc member 101 may be generally defined as a semi-circular arc having a relatively constant radius of curvature defined by the line A-B. Contiguous with outer wall 105 is leading edge wall 125 having a radius of curvature less than outer wall 105. Leading edge wall 125 may be generally defined by the line B-C. Contiguous with leading edge wall 125 is inner convex wall 133 having a radius of curvature that may be generally defined by line C-D. Contiguous with inner convex wall 133 is inner concave wall 131 which in turn is more or less contiguous on the end opposite inner convex wall 133 with outer wall 105 and is generally defined by the line D-A. Inner convex wall 133 and inner concave wall 131 may preferably have similar radii of curvature in opposite directions, which is to say that inner convex wall 133 will extend away from the body of second disc member 101 while inner concave wall will extend inwardly towards the body of second disc member 101. For example, in an embodiment, outer wall 105 may have a radius of curvature of approximately 9 mm, leading edge wall may have a radius of curvature of about 3 mm and inner convex and inner concave walls may each have a radius of curvature roughly 6 mm. It will also be appreciated that the peripheral wall of second disc member may further include additional areas having a smaller radius of curvature at or near point A, for example, to create a more rounded tail portion end of the one-half "yin-yang" shape.

Second disc member upper surface 107 is shown having second disc member upper leading edge surface 115 towards the head portion and second disc member trailing edge surface 109 towards the tail portion of second disc member 101. Positioned on the inner peripheral edge of second disc member 101 is convex inner wall shoulder 145 and concave inner wall shoulder 147 defining in general, a continuous boundary between upper surface 107 and second disc member inner convex wall 133 and between upper surface 107 and inner concave wall 131. Convex inner shoulder 145 and adjacent concave inner wall shoulder 147 may extend more or less from second disc member upper leading edge surface 115 to upper trailing edge surface 109 at second disc member tail wall 161. Positioned adjacent concave inner shoulder 147 on upper trailing edge surface is trailing edge shoulder 159 which extend on the periphery of the tail portion of second disc member 101 until it transitions into outer shoulder 117.

Situated of the surface of inner convex wall 133 and inner concave wall 131, and integrally formed therein is boss 139 defined on one end by second disc inner notch concave end 141 and by second disc member side wall notch tail 157 on its opposite end. Boss 139 is further defined by boss floor 153 on one surface and boss ceiling (not shown) on the opposite surface thereof. It will be understood that boss 139 is shaped to be mateably received by and fit substantially completely within inner notch 140 of first disc member 102 as shown in FIGS. 5 and 6. In other embodiments, boss 139 may be larger or smaller or configured as a tab or series of tabs which may be received partially or completely within corresponding orifices situated on a complimentary disc member to form a congruent discoid structure.

Figure 10:
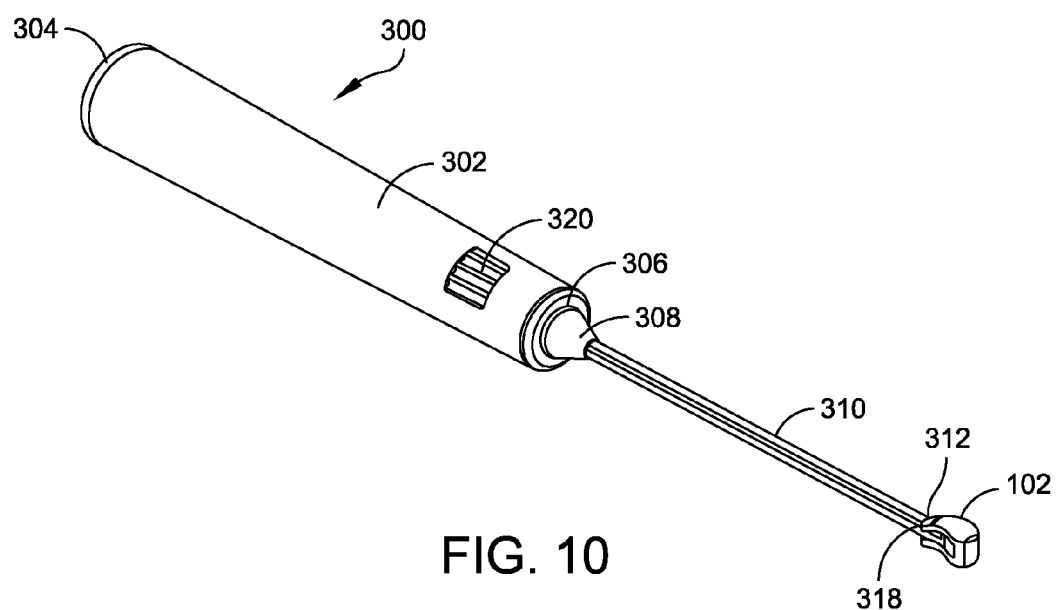
FIG. 10 shows a first disc member mounted on one embodiment of a first member insertion tool of the present invention.

FIG. 10 shows an embodiment of first disc member insertion tool 300 having tool handle 302 for holding the tool and shaft 310 for insertion of first member 102 within the intra spinal space. Handle 302 includes proximal end 304 and shaft end 306. Positioned on shaft end 306 is shaft flange 308 for securing shaft 310 into handle 302. At the distal end of shaft 310 is tool head 312. Tool head 312 and shaft 310 and may further include at least one suture conduit 318 for receiving a suture or wire that is operatively connected to first disc member 102 shown positioned on tool head 312. Positioned within or on handle 302 is tensioner 320. Tensioner 320 is operatively connected to a suture wire or suture cable in communication with one or more orifices of first disc member 102. Tensioner 320 may provide withdrawing tension on of a portion of the suture wire or suture cable and facilitate release of the first disc member 102 from the tool head 312. Tensioner 310 may further include mechanisms for manipulating suture cables or wires which may be placed within the first disc member first suture channel and first disc member second suture channel as generally disclosed herein. Tensioner 320 may take the form of any one of knobs, levers, ratcheted wheels and trigger mechanisms or combinations of the foregoing and need not be limited to the structure shown in the drawing.

First disc member insertion tool 300 and its component parts may be fabricated of various types of metals, metal alloys, plastics, ceramics and other suitable materials including combinations thereof typically used in the fabrication of surgical tools and the like. Preferably, tool 300 is relatively lightweight, durable, easily manipulated and is also inert (i.e. non-reactive to blood and other bodily fluids) and impervious. Preferably still, tool 300 may also be reusable in whole or in part and may therefore preferably be capable of sterilization by autoclave, gases, chemical disinfectants, radiation and other methods known for and useful for sterilizing surgical instruments.

Figure 11:
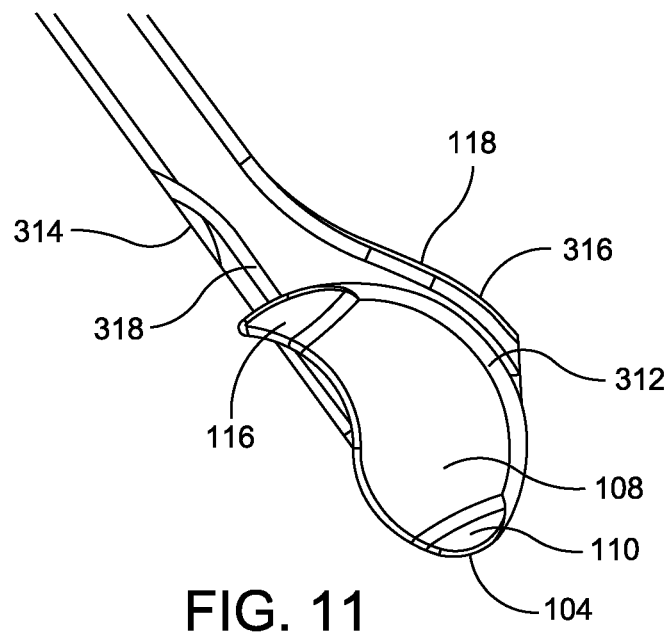
FIG. 11 is a close up view of a first disc member mounted on the distal end of an embodiment of the first member insertion tool shown in FIG. 10.

FIG. 11 shows a close up of tool head 312 located on the distal end of shaft 310 of first disc member insertion tool 300 of FIG. 10. Tool head 312 includes central prong member 314 and side prong member 316. Both prong members act together to provide compressive fitment of first disc member 102. Generally, central prong 314 is rigid or fixed with side prong 316 being somewhat more flexible and providing bias for securely gripping first disc member 102 during manipulation and insertion. Disposed with in the body of central prong 314 is suture conduit 318. Suture conduit 318 may be configured to receive at least on suture cable or wire that is operatively connected to first disc member 102. As will be understood from the drawings and descriptions that follow, the suture cable facilitates removal of first disc member 102 from tool head 312 and proper alignment of first disc member 102 with second disc member 101.

As may be seen from the drawings, located distally on first disc member 102 positioned on tool head 312 is first disc member leading edge upper surface 110 above first disc member leading edge wall 104. Other structures are identified as referenced in the preceding drawings. It will be understood that the leading edge wall and surfaces are designated so as to indicate a preferred orientation of insertion of the disc member into the intradiscal space. The smaller radius of curvature characterizing leading edge wall and surface facilitates placement of the disc segments into the narrow passageway through the annulotomy.

Figure 12:
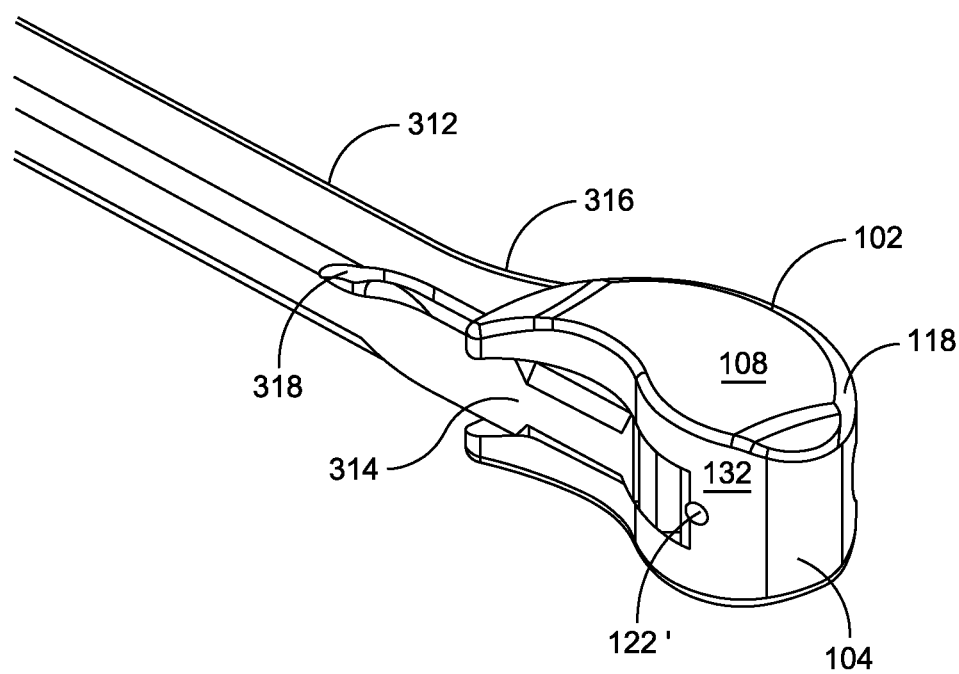
FIG. 12 is an enlarged view of a first disc member mounted on the distal end of an embodiment of the first member insertion tool shown in FIG. 10.

Referring now to FIG. 12 there is shown a side perspective view of tool head 312 and first disc member 102, showing first disc member leading edge wall 104, outer shoulder 118 and first disc member upper surface 108. Central prong 314 substantially occupies the space defined by inner notch on first disc member inner concave side wall 134 and inner convex side wall 132. Positioned on inner convex side wall 132 is first disc member first suture channel 122'. Suture conduit 318 of tool head 312 is in communication with first disc member first suture channel 122' and first disc member second suture channel (not shown).

Figure 13:
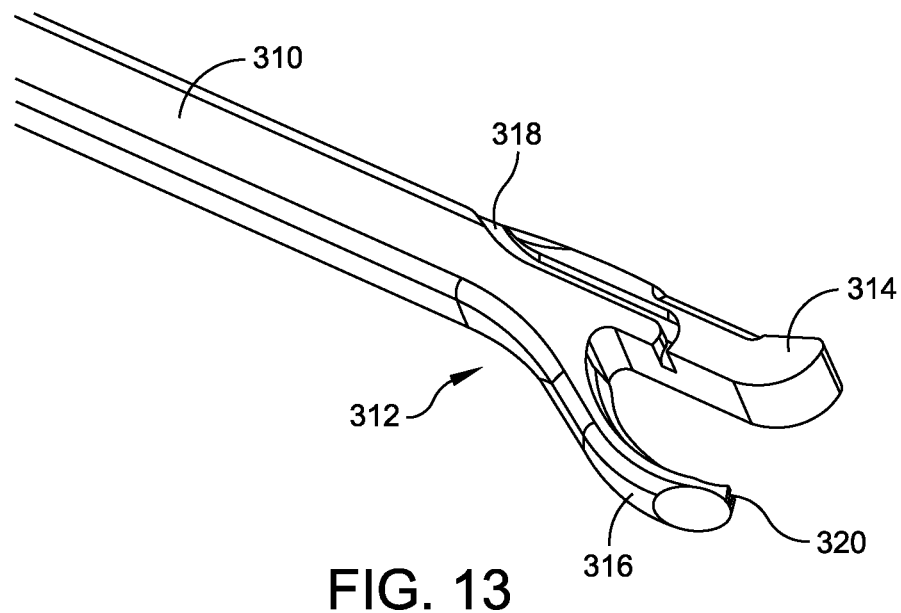
FIG. 13 is an enlarged view of the distal end of an embodiment of the first member insertion tool shown in FIG. 10.

As is shown in FIG. 13, tool head 312 comprises a pair of prongs, central prong 314, and side prong 316. Central prong 314 is generally rigid and is configured so as to substantially fit into the inner notch of a first disc member. Side prong 316 is configured to fit alongside and preferably within the side wall notch of the first disc member. Side prong 316 may be relatively less rigid than central prong 314 so as to operate in concert with each other to form a bias spring to compressively hold a first member securely between the prongs, but in such a way to also allows selective release of the first member. Side prong 316 may also include a U-shaped side prong suture recess 320 for receiving a suture cable or wire (not shown). In one embodiment of the invention, release of the first member from may be accomplished by a suture cable or wire that is operatively connected to the first disc member so that when the suture cable or wire is correctly manipulated, the first disc member will rotate outwardly in a direction away from the side prong using the tip of central prong as a fulcrum or pivot point.

Figure 14:
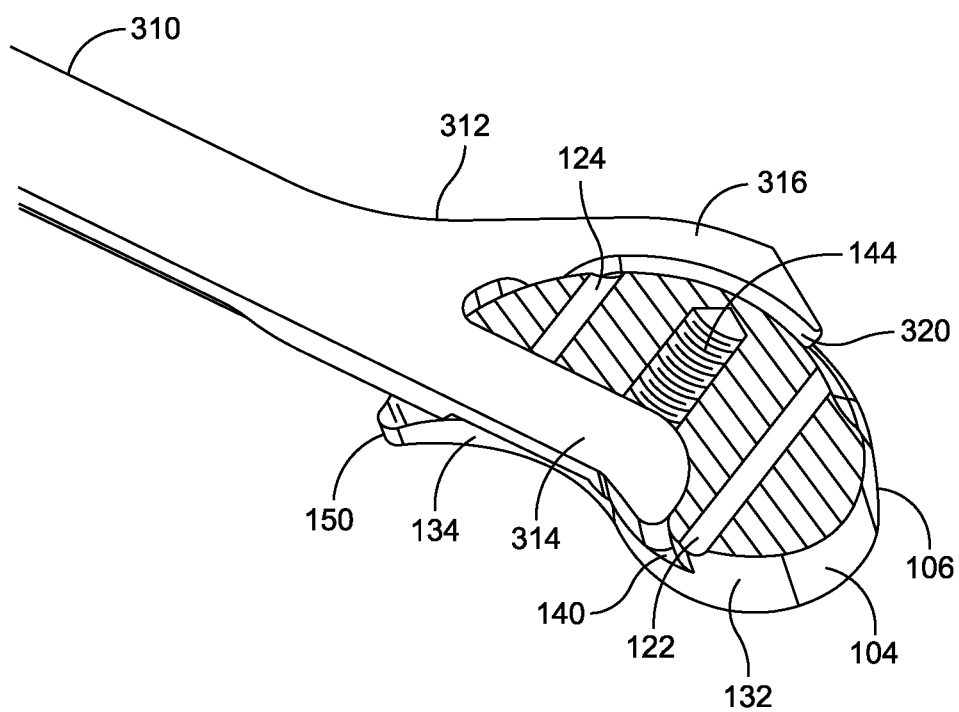
FIG. 14 is an enlarged partial cut away view of a first disc member mounted on the distal end of an embodiment of the first member insertion tool shown in FIG. 10.

FIG. 14 is an enlarged cross sectional view of tool head 312 and first disc member 102 of FIG. 12 showing first disc member leading edge wall 104, outer side wall 106 and first disc member inner convex side wall 132 and inner concave side wall 134. Central prong 314 of tool 300 is shown substantially occupying the space defined by inner notch 140 on first disc member 102 with side prong 316 being positioned within side wall notch 120. Positioned on inner convex side wall 132 are first disc member first suture channel 122' and first disc member second suture channel 124. Located within inner notch 140 is threaded screw aperture 144 which extends radially into the body of first disc member 102. Threaded screw aperture 144 is generally centrally disposed within the body of first disc segment 102 and is adapted to mateably receive a threaded screw or other fastening means. In one embodiment, it will be appreciated that U-shaped suture recess 320 of tool head 312 will have a suture cable or wire (not shown) that is in communication with first disc member first suture channel 122 and first disc member second suture channel 124.

Figure 15:
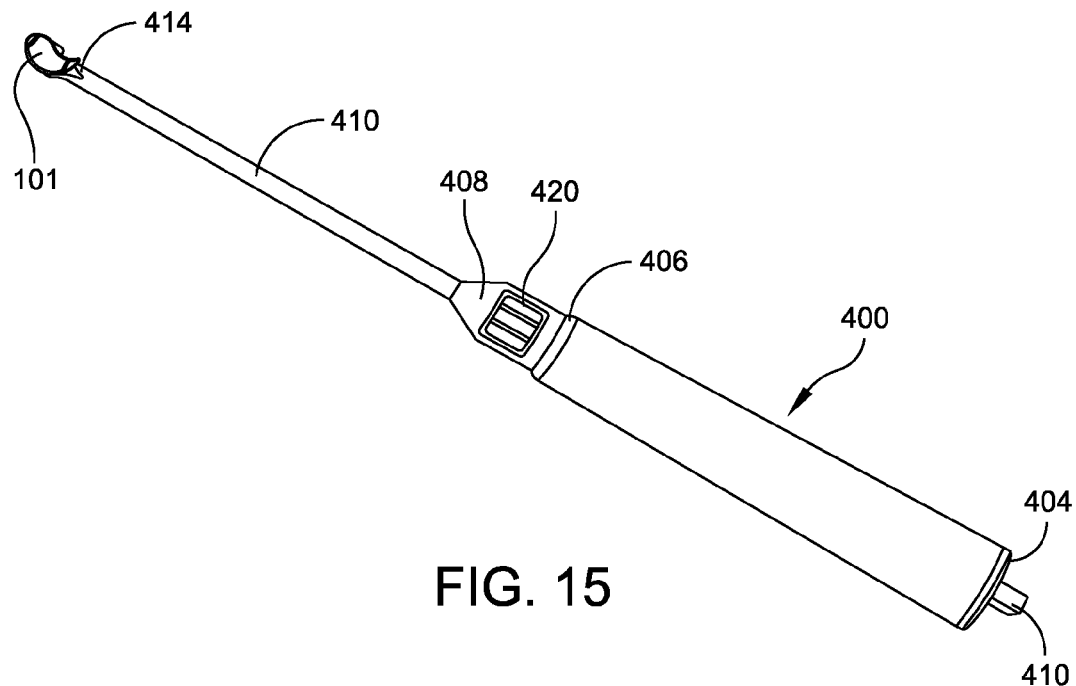
FIG. 15 depicts a side view of a second disc member mounted on one embodiment of a second disc member insertion tool of the present invention.

Referring now to FIG. 15, there is shown a second disc member insertion tool 400 having tool handle 402 for holding the tool and shaft 410 for insertion of second disc member 101 within the intra spinal space. Handle 402 includes proximal end 404 and shaft end 406. Positioned on shaft end 406 is shaft flange 408 for securing shaft 410 into handle 402. At the distal end of shaft 410 is second disc member insertion tool head 412. Shaft 410 is preferably hollow and extends substantially through 402 to proximal end 404. Shaft 410 may have disposed therein a retractable insertion guide pin (shown in FIGS. 17 and 18) which is operatively received by an opening on second disc member 101. Also preferably, shaft 410 may be adapted to receive a screw driver assembly and to deliver a threaded screw through second disc member and into threaded bore of first disc member so as to mechanically join both disc members and to form a congruent discoid shape.

Situated on handle 402 is driver lock wheel 420. Driver lock wheel 420 may be operatively connected to the retractable insertion guide pin and may further include mechanisms for manipulating suture cables or wires which may be placed within the second disc member first suture channel and second disc member second suture channel as generally disclosed herein. Second disc member tool head 412 and shaft 410 and may further include at least one suture conduit (not shown) for receiving a suture or wire that is operatively connected to second disc member 101 shown positioned on tool head 412.

As in the case of first disc insertion tool, second disc member insertion tool 400 and its component parts may be fabricated of various types of metals, metal alloys, plastics, ceramics and other suitable materials including combinations thereof typically used in the fabrication of surgical tools and the like. Preferably, tool 400 is relatively lightweight, durable, easily manipulated and is also inert (i.e. non-reactive to blood and other bodily fluids) and impervious. Preferably still, tool 400 may also be reusable in whole or in part and may therefore preferably be capable of sterilization by autoclave, gases, chemical disinfectants, radiation and other methods known for and useful for sterilizing surgical instruments.

Figure 16:
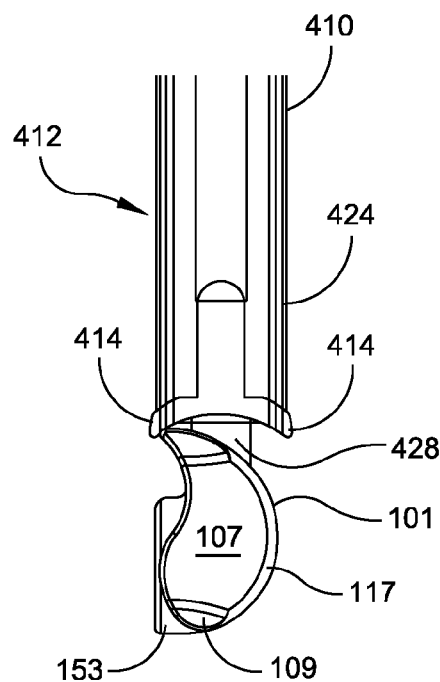
FIG. 16 is a close-up side view of a second disc member mounted on the second disc member insertion tool as shown in FIG. 15.

FIG. 16 shows a close up side view of tool head 412 located on the distal end of shaft 410 of second disc member insertion tool 400 of FIG. 15. Insertion tool 400 is used to place second disc member 101 into position within the annulus, adjacent a first disc member. In one embodiment, shaft 410 may be hollow and is adapted to carry within its central bore a retractable insertion rod 428 having guide pin 422 on its distal end. Guide pin 422 is operatively received by a guide pin orifice on second disc member 101. The guide pin orifice on second disc member 101 may be sized to provide a secure fit that may be readily released by simple remote manipulation. In some embodiments, retractable insertion rod 428 and associated guide pin 430 may be operable manually or they may be operatively connected to driver lock wheel 420 while in other embodiments, second insertion tool may have guide pin 430 integrally formed on second insertion member tool head 412. It will be understood that the second insertion tool head and guide pin 430 may have several different configurations either as separate tools or the tools may be combined with interchangeable heads or other structures which will facilitate insertion, alignment and securing of the first and second disc members. It will also be understood that in other embodiments the features, structures and functions of second disc member insertion tool may be combined with a first disc member insertion tool.

Tool head 412 may also include a pair of outer wall prong members 414 situated on opposite lateral sides of tool head 412. Upon placement and engagement, outer wall prong members 414 will abut against the outer side wall of second disc member 101 and will restrain movement of the second disc member in one direction. Simultaneous tensioning of the suture cables (not shown) which causes movement of the first disc in the opposite direction. This allows the first disc member to move snuggly in alignment with second disc member 101 where they can be secured to each other by a threaded screw or other similar securing structures. As will be apparent from the drawings and descriptions, upon removal of guide pin 430 from guide pin orifice (not shown) of second disc member 101, an interconnected suture cable (not shown) facilitates rotation of second disc member 101 from tool head 412 and allows proper alignment of a first disc member with second disc member 101.

Located distally on first disc member 101 positioned on tool head 412 is second disc member leading edge upper surface 109 above second disc member leading edge wall. It will be understood that the leading edge wall and surfaces are so designated as to indicate a preferred orientation of insertion into the intradiscal space. The smaller radius of curvature characterizing leading edge wall and surface facilitates placement of the disc segments into the narrow passageway through the annulotomy.

Figure 17:
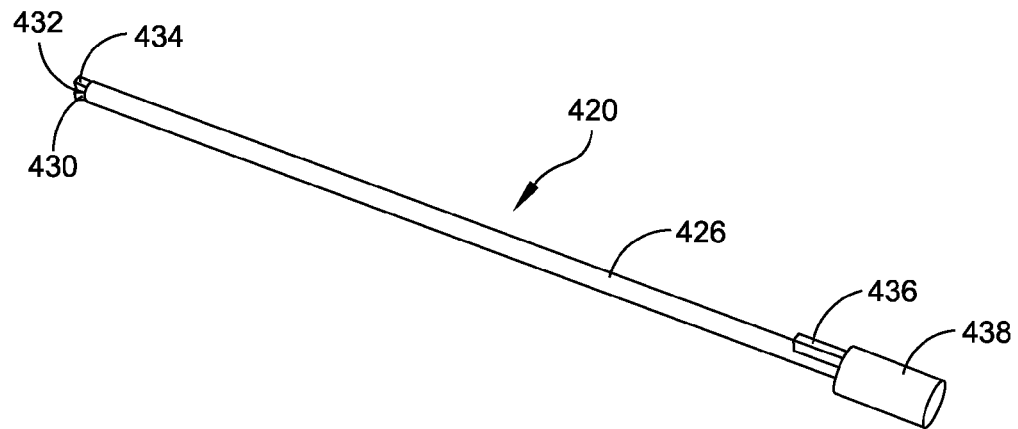
FIG. 17 is a side view of a retractable insertion rod of the second disc member insertion tool of the present invention.

FIG. 17 is a side view of retractable insertion rod 428, having centrally disposed generally cylindrical shaft 426. At the proximal end is shaft head 438, shaft position lock tab 436. Distally on the end of insertion rod 428 is guide pin 430, tapered pin end 432 and arched surface 434. It will be understood that the length and thickness of retractable insertion rod 428 will be complimentary to the second member insertion tool with which it is associated and that it will be fabricated of suitable materials and of suitable construction to enable proper function. Retractable insertion rod 428 may be positioned within tool shaft 410 and can be freely moved up and down the length of the shaft and retracted upon delivery and placement of a second disc element.

Figure 18:
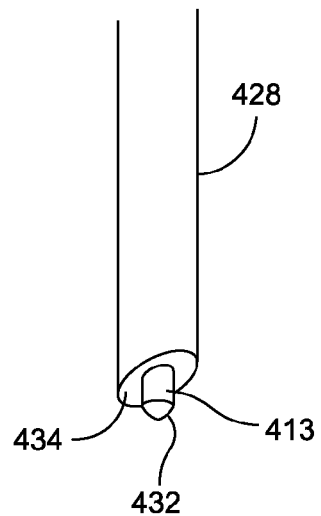
FIG. 18 is a close up bottom perspective view of the distal end of the retractable insertion rod of FIG. 17.

Referring now to FIG. 18 there is shown an enlarged bottom perspective view of retractable insertion rod 428 and guide pin 430. Guide pin 430 is of sufficient length and suitably structured to engage a guide pin orifice formed within a second disc member. At one end of guide pin 430 is tapered pin end 432 for facilitating engagement into a guide pin orifice. At the end opposite tapered pin end 432 is arched surface 434 which provides supplement positive engagement with a second disc member during insertion into the intradiscal space. In the embodiment shown, arched surface 434 has a radius of curvature which is generally complimentary with the portion of a second disc member having the guide pin orifice and thus, it will be appreciated that insertion rod 428 may have to be rotated about its central axis in order to allow proper alignment of arched surface 434 against an outer surface wall portion of a second disc member. In other embodiments, arched surface 434 may have different shapes or appearances depending on the location or locations of the guide pin orifices or it may be entirely absent with guide pin 430 providing the principal insertion force for a second disc member.

Figure 19:
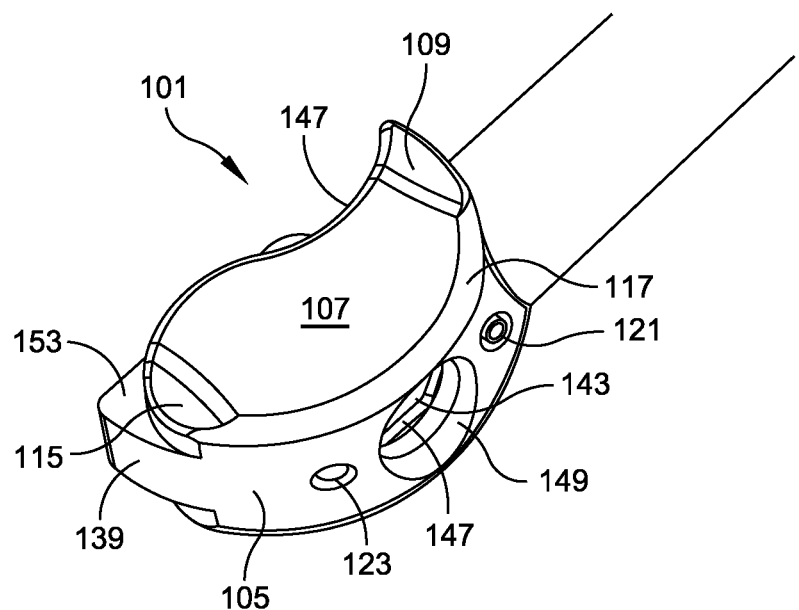
FIG. 19 is a close up view of a second disc member mounted on the end of retractable insertion rod of FIG. 17.

FIG. 19 is an outer side perspective view of second disc member 101 of FIG. 2 engaged on retractable insertion rod 428. Second disc member upper surface 107 is situated centrally on the upper surface of second disc member 101. Generally positioned between second disc member upper surface 107 and outer wall 105 is shoulder 117. Shoulder 117 may be a generally uniform rounded edge to facilitate fit and wear of the endoprosthesis of the present invention when inserted intradiscally. Positioned towards the head portion of second disc member 101 is second disc member upper surface leading edge 115. Positioned posteriorly on the second disc member upper surface 107 towards the tail end of second disc member 101 is second disc member upper surface trailing edge 109. On the peripheral wall opposite shoulder 107 are inner convex and inner concave shoulders 145 and 147, respectively, which may extend more or less from the upper leading edge surface 115 to upper leading trailing edge surface 109.

Situated generally below upper surface shoulder 117 and within second disc member outer side wall 105 are screw aperture 143, screw lock ring 167 and screw recess 149. Positioned at approximately 90° with respect to the bore of screw aperture 143 is inserter pin guide (not shown) engaged by the end of shaft 428. Located generally within second member side wall 105 is second disc member second suture channel 121 and second disc member first suture channel 123. Towards the head portion of second disc member 101 are boss 139 and boss floor 153.

Figure 20:
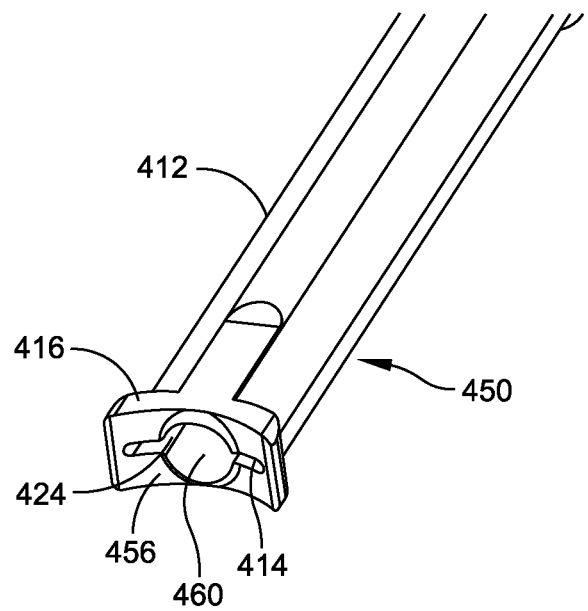
FIG. 20 is an enlarged view the tool head of a second member insertion tool.

FIG. 20 is a front perspective view of the head of second disc member insertion tool 400 having central bore 460. Second tool head 450 comprises tool head face 452 and a pair of tabs 416 having suture channel openings 414 in communication with a corresponding pair of shaft suture channels 424 situated internally on either side of a central bore 460 and which extend substantially the entire length of tool shaft 410. Tool head face 452 of head 450 may be generally curved to fit and abut, in complimentary fashion, onto the curved outer wall surface of a second disc member. Suture channel openings 414 and suture channels 424 are adapted to receive a suture cable loop operatively threaded into corresponding first and second suture channels and which is drawn up into shaft 410. In other embodiments, suture channel openings may be configured as open slits on the face of second tool head and the corresponding pair of shaft suture channels may be configured as channels and may situated externally on either side of and extend the length of tool shaft 410. In yet other embodiments, the shaft suture channels may be omitted in whole or in part, thus allowing the suture cables to be freely accessible outside of the body of tool shaft 410.

Figure 21:
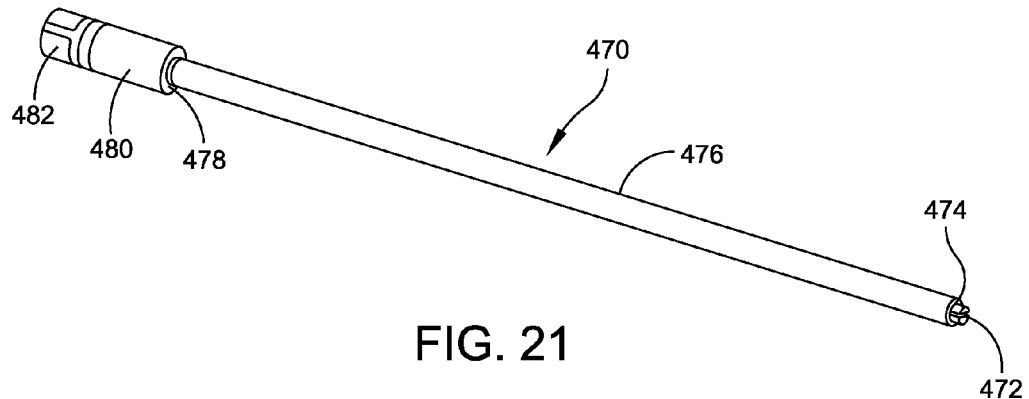
FIG. 21 the screw driver assembly of the second member insertion tool of the present invention.

FIG. 21 is a side view of one embodiment of a screw driver assembly 470 for a second disc member insertion tool of the present invention. At the distal end of shaft 476 of screw driver assembly is hex head insert 472 adjacent lower collar 474. Located near the opposite end of shaft 476 are neck collar 478, shaft ferule 480 and drive knob 482. In some embodiments, screw driver assembly may be inserted within the bore of second disc tool where it will extend through and beyond the tool end to a point where hex head insert 472 can operatively engage a mateable screw head positioned within the threaded screw aperture of a second disc member. In other embodiments, the screw driver assembly may be employed in the absence of using a second disc tool and may be directly engaged with a screw head. Lower collar 474 provides a depth gauge to ensure positive placement of the hex head insert within a screw head to be driven. It will be understood that hex head insert may be smaller or substantially equal to the circumference of shaft 476. Neck collar 478 may be of equal or greater diameter than shaft 476 and generally provides a resting surface for the upper or proximal portion of screw driver assembly on a corresponding shoulder of the second disc member bore. Shaft ferule 480 and drive knob 482 facilitate manipulation of the screw driver assembly and an associated screw. Drive knob 482 may be adjusted manually via finger and thumb manipulation or by manually and electrically operated tools having housings, ratchets or nut drivers adapted to fit drive knob 482.

Figure 22:
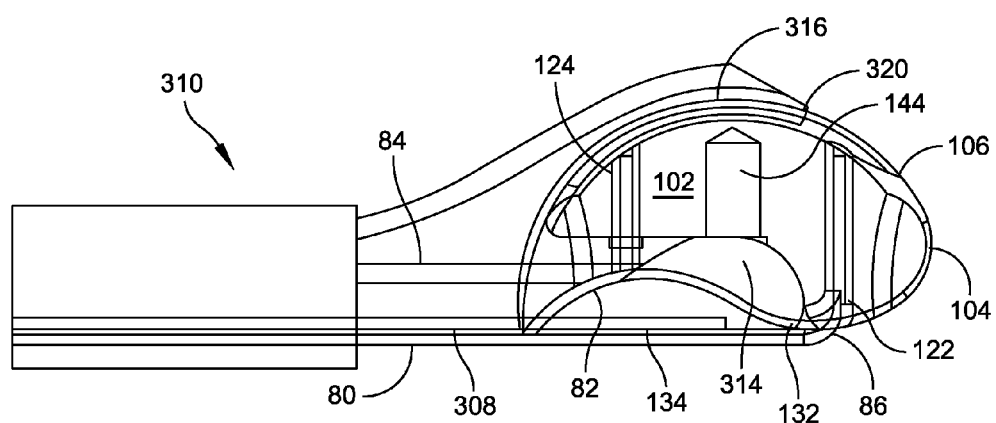
FIG. 22 is a partial cut away view of the shaft portion of the first member positioning tool engaged with one embodiment of the endoprosthetic disc of the present invention.

FIG. 22 is an enlarged cross sectional view of tool head 312 and first disc member 102 of FIG. 12 shown in phantom detail. First disc member includes leading edge wall 104, outer side wall 106 and first disc member inner convex side wall 132 and inner concave side wall 134. Central prong 314 of tool 300 is shown substantially occupying the space defined by inner notch 140 on first disc member 102 with side prong 316 being positioned within side wall notch 120. Positioned on inner convex side wall 132 is first disc member first suture channel 122 and first disc member second suture channel 124.

Disposed with in the body of central prong 314 is suture conduit 318. Within suture conduit 318 and traversing first and second suture channels 122 and 124 respectively, is suture cable 80, operatively connected to first disc member 102. Suture cable 80 is a single length of high tensile strength surgical grade wire having a first end side 84 and a second end side 86 relative to suture cable stopper 82. Suture cable stopper 82 may be a metallic or hard plastic bead having a slightly frusto-conical shape that is larger than the opening of first disc member second suture channel 124. When suture cable 80 is fed through first disc member second suture channel 124, suture cable stopper 82 impedes further movement of the cable in that direction. When mounted on tool 312, U-shaped suture recess 320 will support a portion of suture cable 80 between first disc member first suture channel 122 and first disc member second suture channel 124.

After insertion of first disc member into the spinal space, second end side 86 of suture cable 80 may be manipulated proximally towards the user and away from the direction of insertion of first disc member 102. The movement of suture cable 80 and the resistance of suture cable stopper 82 to proceed on inner concave wall 134 will transfer the force being exerted onto the end of central prong 314, with central prong 314 acting as a pivot point. Continued pulling of second end side 86 in the proximal direction will result in the tail end portion of first disc member 102 to rotating out of and away from inner portion of first tool head 312.

Figure 23:
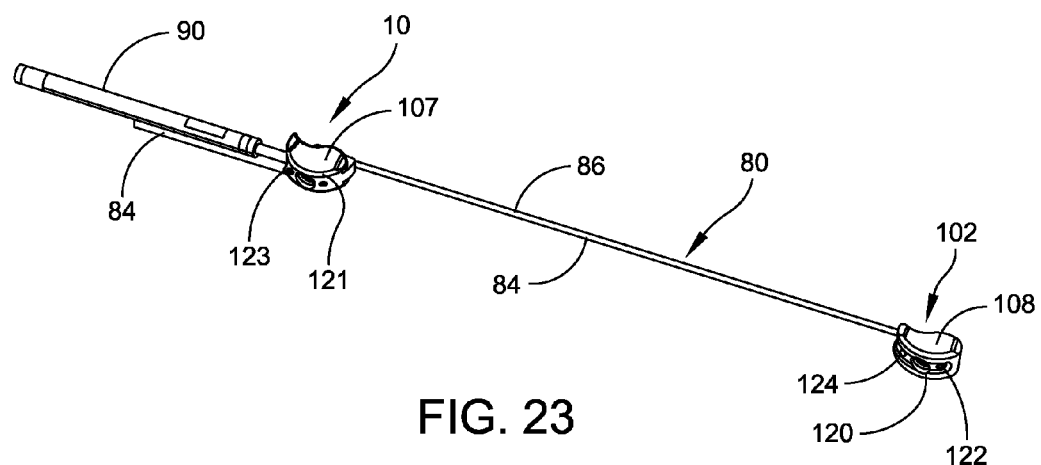
FIG. 23 is a side-perspective view of a first disc member and a second disc member interconnected with a suture cable of the present invention.

FIG. 23 shows one embodiment of first disc member 102 and a second disc member 101 configured for insertion into a spinal space. It will be noted that the features, structures and associated tools for insertion have been detailed with respect to FIGS. 1 through 22 and reference is made to those figures with respect to features and structures numbered in FIG. 23. First disc member 102 and second disc member 101 are both positioned with the head portion of disc members oriented towards the direction of insertion into the intra spinal space. It will also be understood that suture cable 80 traverses second and first disc member in the following general manner. First disc member 102 and second disc member 101 are interconnected by means of suture cable 80 which initiates on suture cable first end side 84 and extends in through the outer wall orifice of second disc member second suture channel 121 and out of the inner wall orifice of second disc member second suture channel 121' continuing on into inner wall orifice of first disc member second suture channel 124' where its forward movement is impeded by suture cable stopper 82. Suture cable 80 then emerges as suture cable second end side 86 exiting from outer wall orifice of first disc member second suture channel 124. Second end side 86 of suture cable 80 then traverses outer wall notch 120 and then enters first disc member outer wall first suture channel orifice 122 and the exits first disc member outer wall first suture channel orifice 122' then continues back towards second disc member 101 and re-enters at inner wall orifice of second disc member first suture channel 123 and exits at outer wall orifice of second disc member first suture channel 123' terminating in termination ferule 90.

It will be appreciated the arrangement and sequence of suture cable wire 80 travel and the order of insertion of first disc member 102 and second disc member 101 is one or several possible arrangement and sequences and may be modified if the order of disc member insertion would be reversed and or if fewer suture channels are present on one or more disc members. The above arrangement and sequence does however allow for optimal suture wire management and proper alignment of first disc member 102 with second disc member 101. It will likewise be appreciated that above arrangement and sequence will permit alignment of the disc members for insertion of a screw or other fastening structures which secure first disc member 102 to second disc member 101.

In one embodiment, the arrangement and sequence of suture cable 80 orientation and the pre-insertion order of disc members 102 and 101 may be pre-assembled as a kit or as an insert to be used with insertion and alignment tools of the types generally disclosed in FIGS. 10 and 15 as well as by other known surgical methods and using other surgical tools without departing from the inventive concepts disclosed herein. In still other embodiments, suture cable 80 and first and second disc members 102 and 101 may be assembled in the general order and sequence just prior to insertion in the intradiscal space.

Figure 24:
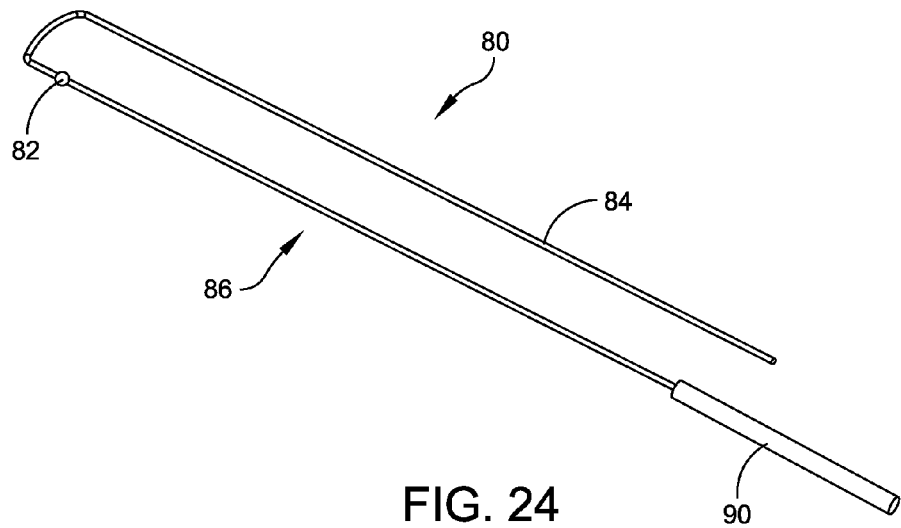
FIG. 24 is a side view of an enlarged suture cable of the present invention.

FIG. 24 is a side perspective view of one embodiment of suture cable 80. First end side 84 is separated roughly mid way from second end side 86 by suture cable stopper 82. Suture cable stopper 82 may be formed integrally with suture cable 80 or it may be preformed and then affixed to suture cable 80 by welding, crimping or bio-compatible adhesive materials. As used throughout, the terms "suture cable" or "suture wire" are intended to be interchangeable and may mean any filament-like element consistent with the present invention. By way of example but not limitation, suture wire and/or the suture cable stopper may comprise a metal (e.g., stainless steel, titanium, Nitinol or other shape memory alloy, etc.) or a plastic (e.g., polypropylene, polyimide, etc.), or other materials or combinations of materials.

It should be noted that the suture wire may have a configuration other than round, e.g., rectangular, square, elliptical, ribbon-like, etc. In this respect it should also be appreciated that a ribbon-like wire could provide increased lateral strength, resulting in more precise guidance as the suture wire passes through the first and second disc members as they are brought in to close proximity and drawn into contact.

The present invention permits a suture wire to be threaded into and through endoprosthetic components which are placed into proximity to bone tissue at a remote surgical site, whereby that suture wire can be used for approximation, positioning and tensioning of the disc components. After proper positioning and alignment, the disc components (i.e. first and second disc members) may be further secured by a threaded fastener or other similar securing structures.

Figure 25:
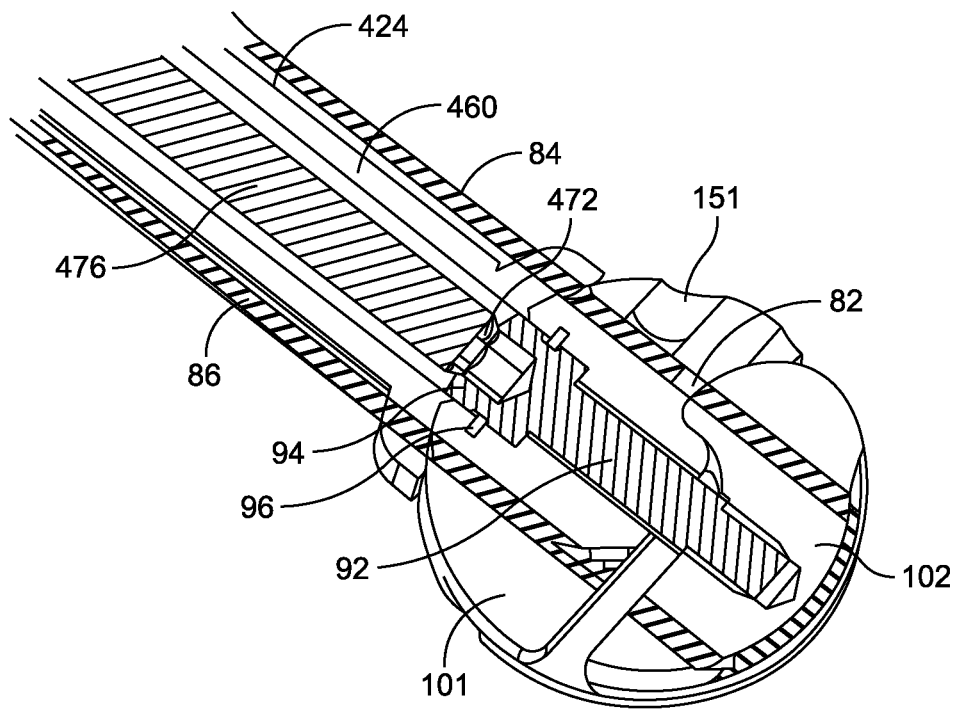
FIG. 25 is a close up perspective cut-away view of the distal shaft portion of the screws driver assembly engaged with a threaded screw inserted in the endoprosthetic disc of the present invention.

FIG. 25 is cross-sectional view of a second tool head and retractable screw driver assembly engaging first and second disc members for delivery of a threaded fastener. Features and structures of disc members 102 and 101 and associated tools for insertion and positioning of disc members have been identified with respect to FIGS. 1 through 24 and are incorporated by reference. Second member insertion tool head 416 is shown in contact engagement with outer wall 105 of second disc member 101. Suture wire 80 having first end section 84 and second end section 86 are tensioned in a direction opposite the direction of second member insertion tool head 416 so as to provide both positive engagement of the tool and to maintain proper alignment of second disc member 101 with first disc member 102. In this manner, the disc members are brought together by the rearward tensioning of the first and second ends of suture wire 80 while the forward force is applied via the head of the second member tool head 416. The relative direction of forces are not unlike those, for example, when pulling the laces of a shoe in one direction while exerting a force in the opposite direction with the foot and leg, although the amount of force in the case of aligning the disc members will likely be considerably different.

Disposed within bore 460 of second tool shaft 412 is screw driver assembly shaft 476 having hex driver tip 472 operatively engaged with mateable screw head 94 positioned atop of threaded screw 92. Threaded screw 92 extends from screw aperture 143 of second disc member 101 into threaded screw aperture 144 of first disc member 102. Screw head 94 is seated within screw aperture recess 149 and may be securely locked in place by screw lock 96 positioned with in screw lock ring 147 of second disc member 101. Screw aperture 143 has a smooth unthreaded bore. Threaded screw aperture 144 of first disc member has a threaded bore complimentary to the threading of screw 92. Engagement of screw 92 by screw driver assembly through unthreaded screw aperture 143 and into threaded screw aperture 144 while maintaining rearward tension on the first and second cable ends and forward force on tool head 416 causes first disc member 102 to be drawn sufficiently into contact with second disc member 101 to be engage screw lock 96 within screw lock recess, thus orienting first and second disc members along complimentary inner walls to form the endoprosthesis of the present invention.

Figure 26:
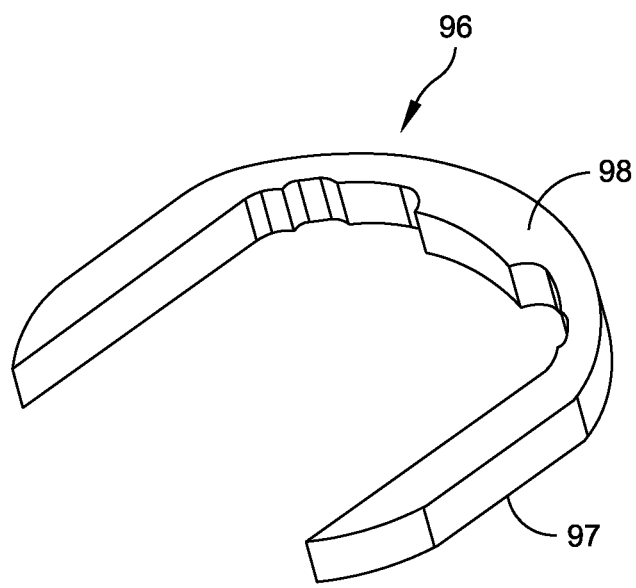
FIG. 26 is an enlarged side perspective view of a lock ring of the present invention.

FIG. 26 is a side perspective view of an embodiment of a screw lock used in one embodiment of the present invention. Screw lock 96 is generally U-shaped having a pair of side arms 97 extending from collar 98. Collar 98 and side arms 97 are adapted to be mounted in a spring-retained holding position upon the screw head or other cylindrical member within a circumferentially extending groove or back of a retaining shoulder, but which may be deformed in a generally radially outward direction to a released position with respect to the groove or shoulder. Screw lock 96 compressively snap fits into a circular groove on screw head of screw (not shown) which may be then engaged with screw lock ring of the second disc member (not shown). Screw lock 96 may be fabricated of metal alloys and other biocompatible materials.

Figure 27:
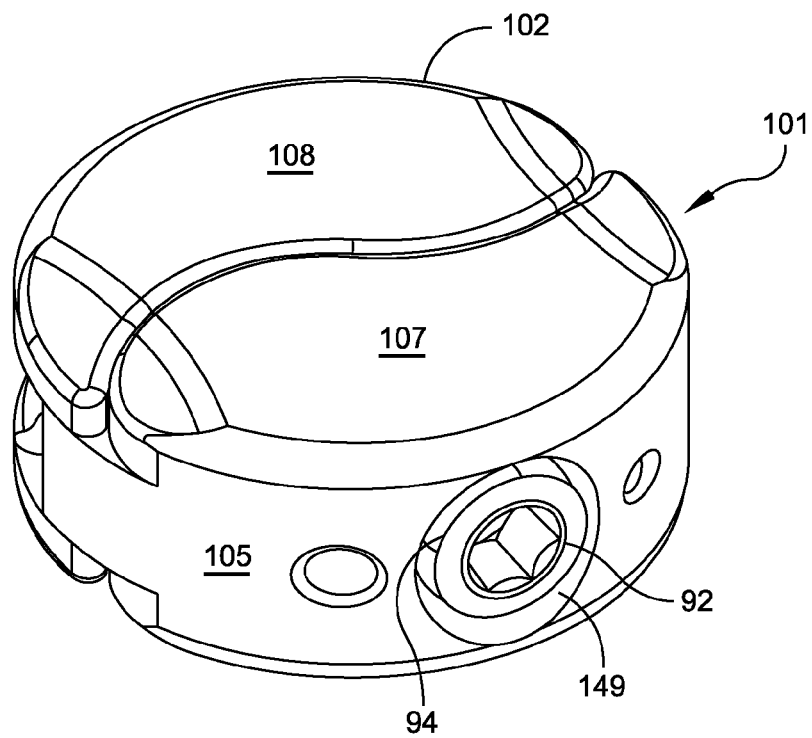
FIG. 27 shows an alternate side perspective view of an the endoprosthetic disc as shown in FIG. 2 of the present invention.

FIG. 27 is a side perspective view of an assembled endoprosthesis of the present invention with the second disc member positioned forward. Features and structures of disc members 102 and 101 previously identified are incorporated by reference. It will be seen from the drawing that screw head 94 of screw 92 is situated at or below second disc member outer wall 105 within screw recess 149. By placing screw head 94 at or below the surface of outer wall 105, with screw 92 locked in place by the screw lock and screw lock recess (not shown), there are no protrusions or projections on outer wall 105 that may abrade or otherwise interfere with the annulus, thus lessening the opportunity for irritation or damage to the annulus when inserted into an intradiscal space.

FIGS. 28-32 is another embodiment of the endoprosthesis of the present invention in which the disc members are a pair of substantially identical mirror image structures. Reference is made to the structures identified in the drawings and their equivalent structures found in the preceding descriptions of the drawings.

Identic disc members 502 includes disc member leading edge wall 504, disc member outer side wall 506 and disc member upper surface 508. Positioned above disc member leading edge wall 504 is disc member upper surface leading edge 510 and disc member upper surface leading edge transition zone 512. Disc member upper surface leading edge transition zone 512 is positioned between and separates disc member upper surface 508 from disc member upper surface trailing edge transition zone 514 and disc member upper surface trailing edge 516. As shown in FIGS. 28-31, transition zones 512 and 514 are positioned on either side of disc member upper surface 508. The transition zones generally define regions on upper surface 508 where the relative height of the upper surface diminishes to a slightly lower height (and therefore overall "thickness") as further defined by disc member upper surface leading edge 510 and disc member upper surface trailing edge 516. The relative positions of transition zones 512 and 514 are not absolute and in some embodiments may be moved forward or backwards relative to the positions shown in FIGS. 28-31.

Positioned adjacent first disc member upper surface 508 is disc member upper surface shoulder 518. Upper surface shoulder 518 may be a smooth rounded surface to improve overall fit and wear characteristics of endoprosthesis 500 and may be configured differently in other embodiments. Situated generally below upper surface shoulder 518 on disc member outer side wall 106 is side wall notch 520. Side wall notch 520 may be a groove or depression adapted for receiving one embodiment of surgical tool or other apparatus for delivering disc member 502 to a desired location. Located generally within side wall notch 520 is disc member first suture channel 522 and disc member second suture channel 524. In other embodiments (not shown), disc member second suture channel may be optionally omitted or may be positioned directly on side wall 506.

Figure 28:
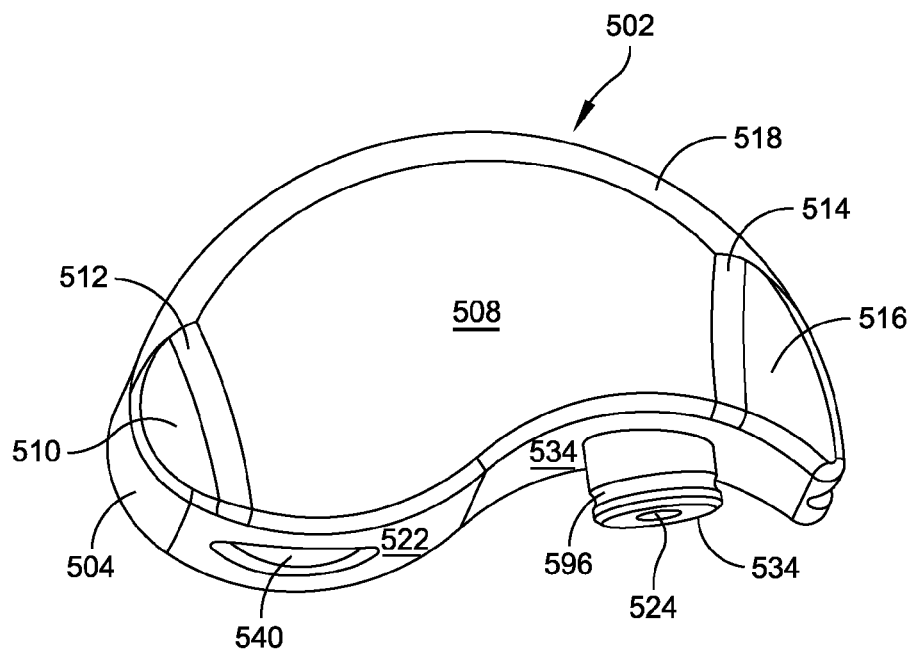
FIG. 28 is a top perspective view of an alternate embodiment of a disc member of the present invention.
Figure 29:
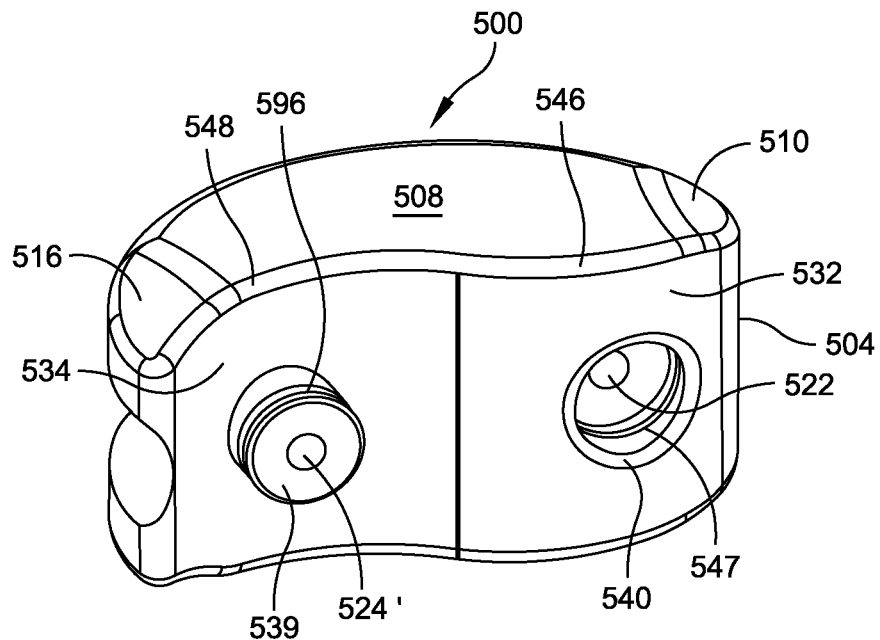
FIG. 29 is a side perspective inner wall view of the disc member of FIG. 28.
Figure 30:
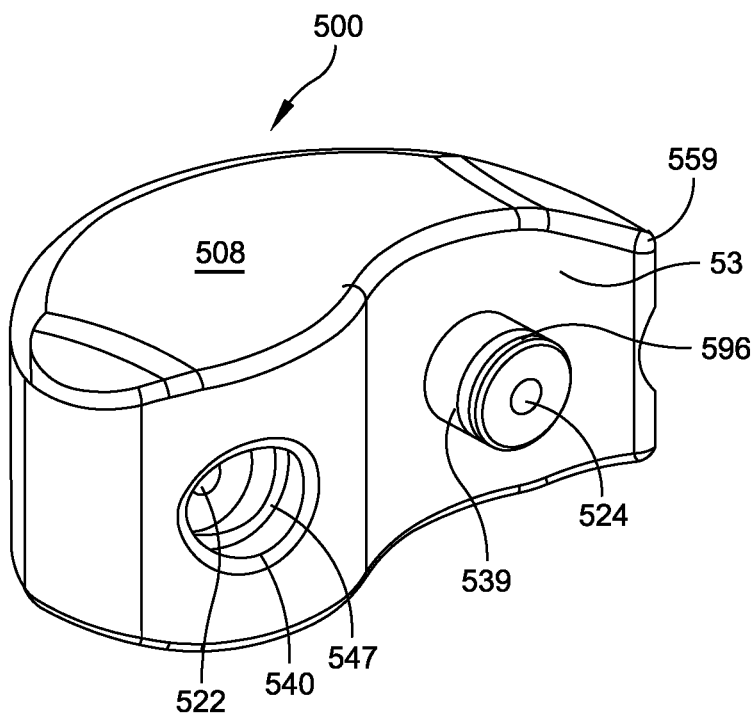
FIG. 30 is a distal side perspective view of the disc member shown in FIG. 28 rotated 180°.
Figure 31:
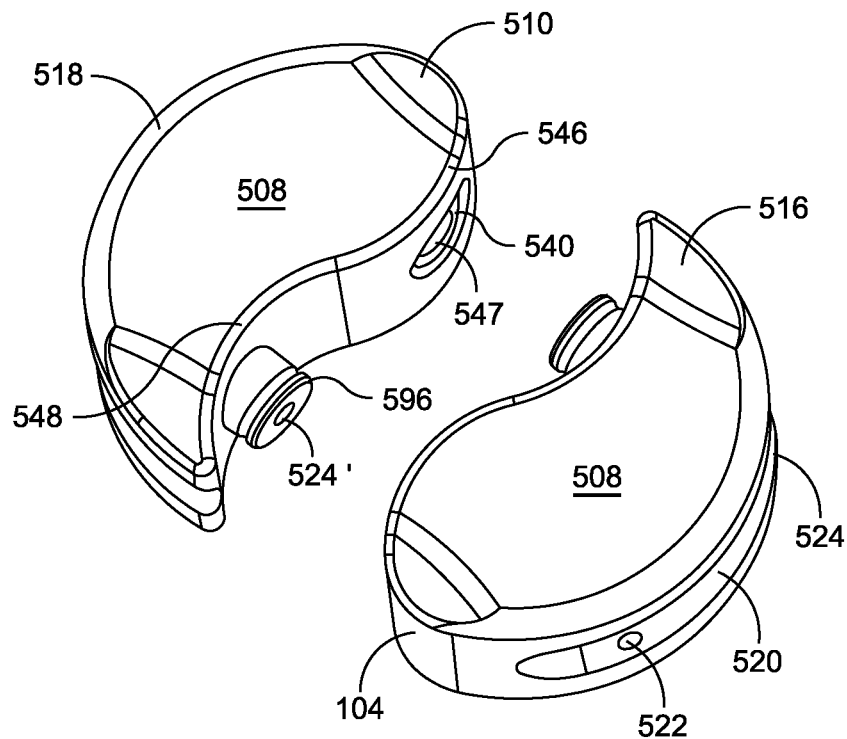
FIG. 31 is a top perspective view of a pair of disc members shown in FIG. 28.
Figure 32:
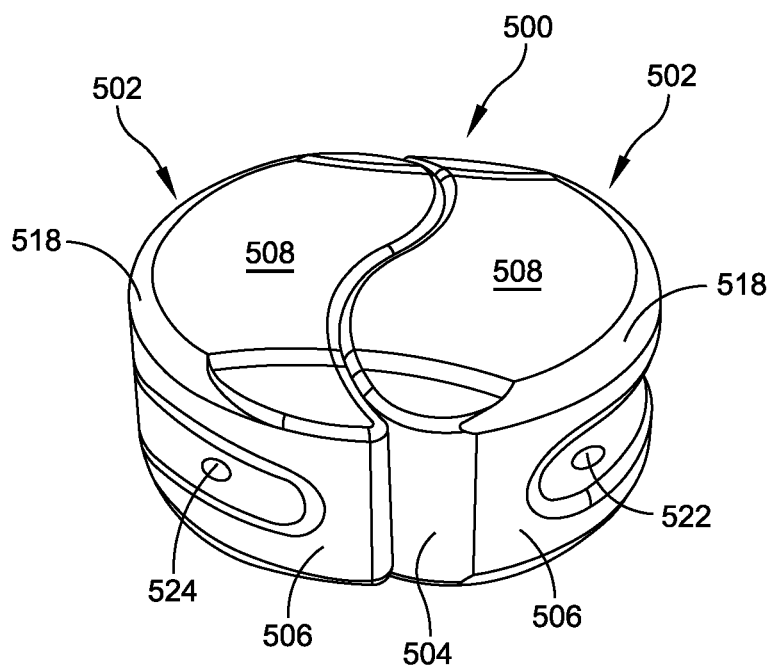
FIG. 32 is a side perspective view of an alternate embodiment of the endoprosthesis of the present invention.

Referring now to FIGS. 28 and 29, there are shown top perspective views of disc member 502. Disc member has a surface shape substantially similar to one-half of the "yin-yang" symbol generally defined a continuous upper and lower periphery and further defined by outer wall shoulder 518, leading edge shoulder 560, convex inner wall shoulder 546, concave inner wall shoulder 548 and trailing edge shoulder 558.

Outer wall 506 may be generally defined as a semi-circular arc having a relatively constant radius of curvature defined by the line A-B. Contiguous with outer wall 506 is leading edge wall 504 having a radius of curvature less than outer wall 502. Leading edge wall 504 may be generally defined by the line B-C. Contiguous with leading edge wall 504 is inner wall convex wall 532 having a radius of curvature that may be generally defined by line C-D. Contiguous with inner convex wall 504 is inner concave wall 534 which in turn is more or less contiguous on the end opposite inner convex wall 532 with outer wall 506 and is generally defined by the line D-A. Inner convex wall 532 and inner concave wall 534 will generally have similar radii of curvature in opposite directions, which is to say that inner convex wall 532 will extend away from the body of disc member 502 while inner concave wall will extend towards the body of first disc member 502. For example, in an embodiment, outer wall 506 may have a radius of curvature of approximately 9 mm, leading edge wall may have a radius of curvature of about 3 mm and inner convex and inner concave walls may each have a radius of curvature roughly 6 mm. It will also be appreciated that the peripheral wall of first disc member may further include additional areas having a smaller radius of curvature at or near point A, for example, to create a more rounded tail portion end of the one-half "yin-yang" shape.

Disc member upper surface 508 is more or less situated centrally on the upper surface of disc member 502. Generally positioned between first disc member upper surface 508 and outer wall 506 is shoulder 518. In the embodiment shown shoulder 518 may be a generally uniform rounded edge to facilitate fit and wear of the endoprosthesis of the present invention when inserted intradiscally; however, it will also be appreciated that shoulder 518 may be optionally absent or non-uniform in its configuration and may take other forms with a greater or lesser rounded edge surface. Positioned towards the head portion of disc member 502 are disc member upper surface leading edge 510 and disc member upper surface leading edge transition zone 512. Disc member upper surface leading edge transition zone 512 is positioned between disc member upper surface 508 and disc member leading edge surface 510. Positioned posteriorly on the disc member upper surface 508 towards the tail end of disc member 502 are upper surface trailing edge transition zone 514 and disc member upper surface trailing edge 516. On the peripheral wall opposite shoulder 518 are inner shoulders 546 and 548 which may extend more or less from the upper leading edge surface 510 to upper leading trailing edge surface 516.

Inner convex wall 532 includes boss chamber 540 having disposed centrally therein first suture channel 522. Adjacent inner concave wall includes boss 539 having disposed centrally therein second suture channel 524. Boss chamber 540 is extends into the body of disc member 502 to a depth sufficient to mateably receive boss 539 of a complimentary disc member. In the embodiment shown boss 539 is a generally cylindrical member extending from inner concave wall 534 and boss chamber 540 is a generally cylindrical bore having a circumferential opening and depth roughly that of boss 539. Within boss chamber 540 is annular groove 567 which receives boss ring 596 in a compressive fit manner. In one embodiment annular groove 567 and boss ring 596 are both slightly beveled in a complimentary fashion so as to enable easier entry and association of boss 539 and boss ring 596 into boss chamber 540 and annular ring 596 and to create significant resistance to their disengagement. In other embodiments, boss 539 and boss chamber 540 may be positioned on inner convex wall 532 and inner concave wall 534 respectively.

It will be appreciated that identic disc members 502 may be delivered into intradiscal space using the first member tool of the present invention and that this embodiment does not require a separate tool for positioning and aligning the members for a threaded screw or other fastening structure. Instead, both disc members may be delivered with the same tool which may be a modified first member insertion tool referenced in FIGS. 10 through 14. It will likewise be understood that the suture cable 80 disclose herein will traverse the identic disc members in the following general manner with reference to a close or proximal disc member and a further away or distal disc member. The distal disc member in this regard may also be considered the initial or first disc member inserted into a patient.

Disc members 502 are interconnected by means of suture cable 80 which initiates on suture cable first end side 84 and extends in through an outer wall orifice of proximal disc member second suture channel 521 and out of the inner wall orifice of second disc member second suture channel 521' continuing on into inner wall orifice of a distal disc member second suture channel 524' where its movement is impeded by suture cable stopper 82, suture cable 80 then emerges as suture cable second end side 86 exiting from outer wall orifice of first disc member second suture channel 524. Second end side 86 of suture cable 80 then traverses outer wall notch 520 of distal disc member and then enters distal disc member outer wall first suture channel orifice 522 and the exits distal disc member outer wall first suture channel orifice 522' then continues back towards proximal disc member and re-enters at inner wall orifice of proximal disc member first suture channel 523 and exits at outer wall orifice of proximal disc member first suture channel 523 terminating in termination ferule 90. This configuration permits a suture wire to be threaded into and through endoprosthetic components which are placed into proximity to bone tissue at a remote surgical site, whereby the suture wire can be used for approximation, positioning and tensioning of the disc components together by manipulating the first and second ends of suture wire 80 so as to draw the members together in the manner disclosed herein.

In this respect, disc member insertion tool head will be in contact engagement with outer notch 506 of the proximal disc member. Suture wire 80 having first end section 84 and second end section 86 may both be then tensioned in a direction opposite the direction of force of the insertion tool so as to provide positive engagement of the tool in one direction (i.e. away from the tool) and by simultaneously tensioning and drawing up the suture cable in an opposite direction (i.e. towards the tool), thus maintaining both proper alignment and closure of the disc members to each other to form a congruent spinal disc insert.

The following is one example of an operative technique for insertion of a modular nucleus pulposus endoprosthesis of the present invention. The patient is positioned in a prone position on a cantilevered radiolucent operating table on which has been placed a kambin frame, and/or bolsters, and/or a "Jackson" table. After standard prep and sterile drape a midline incision is made over the spinous processes of the lumbar vertebra at the appropriate lumbar level with or without image intensification for localization of the appropriate level. A subperiostial dissection can be carried out either bilaterally out to the facet joints or unilaterally as in the standard approach for a laminotomy and disc excision and/or laminectomy and posterior lumbar interbody fusion (PLIF). A laminotomy is created at the interspace between the vertebrae. Alternatively, a hemilaminectomy can be carried out. If it is necessary to do a medial facetectomy for exposure, care is taken to preserve at least ½ of the facet joint. Hemostasis is established and maintained within the spinal canal using bipolar electric cautery. The dura and descending nerve root are carefully retracted to the midline to identify the disc space.

Once the disc space is identified careful retraction is used to hold the dura and descending nerve root to the midline. An annulotomy is made measuring approximately 6 to 7 mm. Any sequestered or herniated disc material is excised; the disc space is entered and cleared of remaining nucleus pulposus tissue using pituitary rongeurs and/or upbiting curettes in a technique similar to that employed for a PLIF. Following complete evacuation of nucleus pulposus adequacy of space is confirmed by inserting a balloon bone tamp, similar to a "kyphoplasty" and expanding the balloon with radiopaque fluid. AP and lateral image views are used to confirm the adequacy of the discectomy. A lamina spreader is then inserted between the spinous processes of the vertebra at that level to facilitate the insertion of the components of the modular nucleus through the annulotomy.

Procedure for modular nucleus replacement through annulotomy: A first disc member is attached to first disc member insertion tool and the suture cables appropriately tensioned. The first disc member is inserted, large end first with concavity oriented laterally, by gently tapping through the annulotomy while retracting the dura and nerve root. Once the first disc member has been inserted it is rotated out by manipulating the cable handle on the insertion tool and the first member insertion tool carefully removed. A second disc member is then secured to a second disc member insertion tool, the suture cables appropriately tensioned and the second disc member is gently tapped through the annulotomy into position. At this point the second disc member insertion tool becomes the tool to interlock the components. The center post of this tool is removed. The cables are tensioned against the end of the insertion tool to bring the screw holes into alignment. Through the center of the tool, the depth gauge is inserted to insure that the screw aperture is clear and alignment of the components is appropriate. The interlocking screw is then inserted through the center of the locking tool and tightened with the torque wrench. The ferrule end of the tensioning cable is then released from the cable handle and the cable gently pulled through the instrument removing it from the implant and from the disc space. Position of the assembled implant is confirmed on AP and lateral image views.

The dura and the nerve root are allowed to return to anatomical position. After securing hemostasis, the laminectomy defect is covered with either a piece of gelfoam or a piece of fat harvested from the incision. The wound is then closed in layers using interrupted 0 vicryl for the fascia layer, 2-0 vicryl for the subcutaneous tissue and 4-0 monocryl interarticular technique for the skin. A dry sterile dressing is applied and secured with tape or opsite. The patient is then carefully turned to the supine position and transferred to the recovery room on stretcher or orthopaedic bed.

While one aspect of the present invention is insertion of the disc segments posteriorly, it will be understood that the endoprosthesis of the present invention may also be inserted via conventional anterior disc repair and/or replacement. In such instances, the constrictions and limitations of posterior insertion may be avoided and the endoprosthesis may also be preassembled prior to insertion and placed within the annulus of the spinal disc after removal of the nucleus pulposus.

It will also be appreciated that in other embodiments the disc segments may be inserted and aligned using the modified PUF procedure and that the disc segments may be aligned within, and held in place by the constriction of the annulus without any optional fasteners due to the complimenting cam-like shapes which prevent lateral slippage of one insert over the other within the annulus.

From the foregoing detailed description and examples, it will be evident that modifications and variations can be made in the devices and methods of the invention without departing from the spirit or scope of the invention. Therefore, it is intended that all modification's and verifications not departing from the spirit of the invention come within the scope of the claims and their equivalents.

From the foregoing detailed description and examples, it will be evident that modifications and variations can be made in the devices and methods of the invention without departing from the spirit or scope of the invention. Therefore, it is intended that all modifications and verifications not departing from the spirit of the invention come within the scope of the claims and their equivalents.

I claim:

1. An endoprosthesis for insertion into the annulus of a spinal disc comprising:
   a generally discoid assembly having latitudinal and longitudinal axes, said discoid assembly comprised of biocompatible materials and formed by a plurality of complimentary teardrop shaped bodies, each of said bodies having a curving pointed tip end and a blunt end opposite said pointed tip end mateably arranged along a common "s" shaped border in a congruent manner, said discoid assembly having upper and lower convex surfaces, said upper and lower convex surfaces having a curvature that generally corresponds with a pair of a human vertebral segments.

2. The endoprosthesis of claim 1 wherein said bodies are configured to join together and fit within the annulus upon implantation therein.

3. The endoprosthesis of claim 1 wherein said bodies further comprise a peripheral outer wall having a fixed radius of curvature and an inner wall having at least one concave portion and at least one convex portion adjacent thereto wherein said at least one concave portion is connected at one end to said outer wall and at least one adjacent convex portion is connected to the other end.

4. The endoprosthesis of claim 1 wherein the biocompatible materials are selected from the group comprising orthopedic metal alloys, biocompatible ceramics, biocompatible silicone elastomers and combinations thereof.

5. An endoprosthesis for insertion into an annulus of a spinal disc, said endoprosthesis comprising:
   a body comprised of biocompatible materials having a substantially discoid shape, the body including a first body portion and a second body portion, the first body portion having a teardrop shape including a curving pointed tip end and a rounded end and having a first peripheral mating face including a variable radius of curvature and a peripheral outer wall having a fixed radius of curvature, the second body portion having a teardrop shape including a curving pointed tip end and a rounded end and having a second peripheral mating face including a variable radius of curvature and a peripheral outer wall having a fixed radius of curvature substantially identical to the radius of curvature of said first portion wherein said second peripheral mating face is complementary with said first mating face.

6. The endoprosthesis of claim 5, wherein one of the first or second mating faces has a convex portion and the other of the first or second mating faces has a concave portion, the convex portion configured to matingly engage with the concave portion along a common "s" shaped border.

7. The endoprosthesis of claim 5, wherein the first mating face of the first body portion has a first convex portion and a first concave portion and the second mating face has a second convex portion and a second concave portion, and wherein the first convex portion configured to matingly engage with second concave portion and the first concave portion configured to matingly engage with second convex portion.

8. The endoprosthesis of claim 7, wherein each of said bodies has a curved outer peripheral face having a radius of curvature and wherein the first and second convex and concave mating faces having a radius of curvature which is less than the radius of curvature of the outer face.

9. The endoprosthesis of claim 7, wherein said radius of curvature of the first and second convex and concave mating surfaces form a substantially partially circular shape when mateably engaged.

10. The endoprosthesis of claim 9, wherein said variable radius of curvature of the first and second convex and concave mating surfaces of each of said bodies form substantially partially elliptical shapes.

11. The endoprosthesis of claim 7, wherein the radius of curvature of the peripheral outer face is greater than the radius of curvature of the first and second convex and concave mating inner surfaces.

12. The endoprosthesis of claim 5, wherein said radius of curvature of said outer peripheral faces is substantially constant forming a substantially partially circular shape when said body portions are mateably engaged.

13. The endoprosthesis of claim 5, wherein said variable radius of curvature of the inner peripheral face forms a substantially partially elliptical shape.

14. The endoprosthesis of claim 5, wherein the body portions are configured to join together and fit within the annulus upon implantation therein.

15. The endoprosthesis of claim 5 wherein the biocompatible materials are selected from the group comprising orthopedic metal alloys, biocompatible ceramics, biocompatible silicone elastomers and combinations thereof.

\* \* \* \* \*